(12) United States Patent
Zhang

(10) Patent No.: US 10,092,043 B2
(45) Date of Patent: Oct. 9, 2018

(54) BRA AND BRA COMPONENTS

(71) Applicant: Regina Miracle International (Group) Limited, Kwai Chung (HK)

(72) Inventor: Wenbo Zhang, Kwai Chung (HK)

(73) Assignee: Regina Miracle International (Group) Limited, Kwai Chung (HK)

(*) Notice: Subject to any disclaimer, the term of this patent is extended or adjusted under 35 U.S.C. 154(b) by 0 days.

(21) Appl. No.: 14/718,862

(22) Filed: May 21, 2015

(65) Prior Publication Data
US 2015/0335078 A1 Nov. 26, 2015

(30) Foreign Application Priority Data

May 26, 2014 (WO) ................ PCT/CN2014/000532
Jan. 22, 2015 (CN) ........................... 2015 1 0032889

(51) Int. Cl.
*A41C 3/00* (2006.01)
*A61B 5/00* (2006.01)
(Continued)

(52) U.S. Cl.
CPC .......... *A41C 3/0064* (2013.01); *A41C 3/0007* (2013.01); *A41C 3/122* (2013.01);
(Continued)

(58) Field of Classification Search
CPC ......... A41C 3/00; A41C 3/144; A41C 3/0205; A41D 13/008; A41D 13/1236
(Continued)

(56) References Cited

U.S. PATENT DOCUMENTS 5,621,188 A * 4/1997 Lee .......................... A61N 1/14
174/390
5,690,537 A * 11/1997 Kalmus ................ A41D 13/008
2/267
(Continued)

FOREIGN PATENT DOCUMENTS

CN 201394014 Y 2/2010
CN 101854852 A 10/2010
(Continued)

OTHER PUBLICATIONS

"International Search Report and Written Opinion of the International Search Authority", dated Mar. 4, 2015, issued in counterpart International Patent Application No. PCT/CN2014/000532.
(Continued)

*Primary Examiner* — Gloria Hale
(74) *Attorney, Agent, or Firm* — Kaplan Breyer Schwarz, LLP

(57) ABSTRACT

A bra to enable monitoring of a wearer's heart rate. There is provided a bra comprising a left breast cup; a right breast cup; and a center gore attached between the left and right breast cups. Each of the left and right breast cups comprises a lower edge region which is shaped to follow the shape of a wearer's breast and is shaped to be positioned below a wearer's breast to support the breast, and wherein the lower edge region comprises an electrically conductive fabric layer on the inner surface for contact with the user's skin. The center gore comprises an attachment area for attachment of a transmitter and an electrically conductive pathway from the electrically conductive fabric of the lower regions of the breast cups to the attachment area. Bra components for providing electrical pathways are also provided.

21 Claims, 20 Drawing Sheets

(51) Int. Cl.
*A41C 3/12* (2006.01)
*A41D 13/12* (2006.01)
*A61B 5/024* (2006.01)
*A61B 5/0408* (2006.01)

(52) U.S. Cl.
CPC .......... *A41D 13/1281* (2013.01); *A61B 5/024* (2013.01); *A61B 5/6804* (2013.01); *A61B 5/0006* (2013.01); *A61B 5/02438* (2013.01); *A61B 5/02444* (2013.01); *A61B 5/0408* (2013.01)

(58) Field of Classification Search
USPC ........ 450/1, 93, 58, 41, 43, 47–51; 600/388, 600/389, 301, 382, 390, 393, 547
See application file for complete search history.

(56) References Cited

U.S. PATENT DOCUMENTS

| | | | | |
|---|---|---|---|---|
| 6,488,564 | B1* | 12/2002 | Gray | A41C 3/00 450/1 |
| 6,665,877 | B1* | 12/2003 | Gray | A41C 3/00 2/400 |
| 7,474,910 | B2* | 1/2009 | Hassonjee | A61B 5/0245 600/386 |
| 9,210,956 | B2* | 12/2015 | Bolt | A41C 3/005 |
| 2004/0009731 | A1* | 1/2004 | Rabinowicz | A41D 13/1236 442/316 |
| 2006/0135863 | A1* | 6/2006 | Birnbaum | A61B 5/0002 600/388 |
| 2008/0045808 | A1 | 2/2008 | Hassonjee et al. | |
| 2008/0077042 | A1* | 3/2008 | Feldkamp | A61B 5/103 600/547 |
| 2008/0140155 | A1* | 6/2008 | Pilla | A61N 2/02 607/50 |
| 2008/0143080 | A1* | 6/2008 | Burr | D04B 1/14 280/495 |
| 2008/0208029 | A1* | 8/2008 | Thijs | A61B 5/6804 600/388 |
| 2008/0287769 | A1* | 11/2008 | Kurzweil | A61B 5/0408 600/388 |
| 2008/0287770 | A1* | 11/2008 | Kurzweil | A61B 5/0408 600/388 |
| 2009/0112079 | A1* | 4/2009 | Hassonjee | A61B 5/0245 600/388 |
| 2009/0181599 | A1* | 7/2009 | Farmer | A41B 17/00 450/39 |
| 2010/0105285 | A1* | 4/2010 | Shao | A41C 3/144 450/56 |
| 2011/0004088 | A1* | 1/2011 | Grossman | A61B 5/04085 600/382 |
| 2013/0053674 | A1* | 2/2013 | Volker | A61B 5/04085 600/389 |
| 2013/0281795 | A1* | 10/2013 | Varadan | A61B 5/02055 600/301 |
| 2013/0281815 | A1* | 10/2013 | Varadan | A61B 5/04085 600/388 |
| 2013/0338472 | A1* | 12/2013 | Macia Barber | A61B 5/04085 600/388 |
| 2014/0012145 | A1* | 1/2014 | Kurzweil | A61B 5/0408 600/483 |
| 2014/0206949 | A1* | 7/2014 | Lucas | G06F 19/3418 600/301 |
| 2015/0133030 | A1* | 5/2015 | Bolt | A41C 3/005 450/93 |
| 2015/0297135 | A1* | 10/2015 | Shoshani | A61B 5/0408 600/388 |
| 2015/0305676 | A1* | 10/2015 | Shoshani | A61B 5/0408 600/388 |
| 2016/0058079 | A1* | 3/2016 | Sexton | H05K 9/009 2/455 |
| 2017/0188638 | A1 | 7/2017 | Liu | |

FOREIGN PATENT DOCUMENTS

| | | |
|---|---|---|
| CN | 203028135 U | 7/2013 |
| EP | 1916323 A2 | 4/2008 |
| WO | 2004006700 A1 | 1/2004 |

OTHER PUBLICATIONS

"Chinese Office Action", Issued in Counterpart Chinese Patent Application 2017121502143710, dated Dec. 20, 2017, 16 pp.

* cited by examiner

FIG. 1 *(Prior Art)*
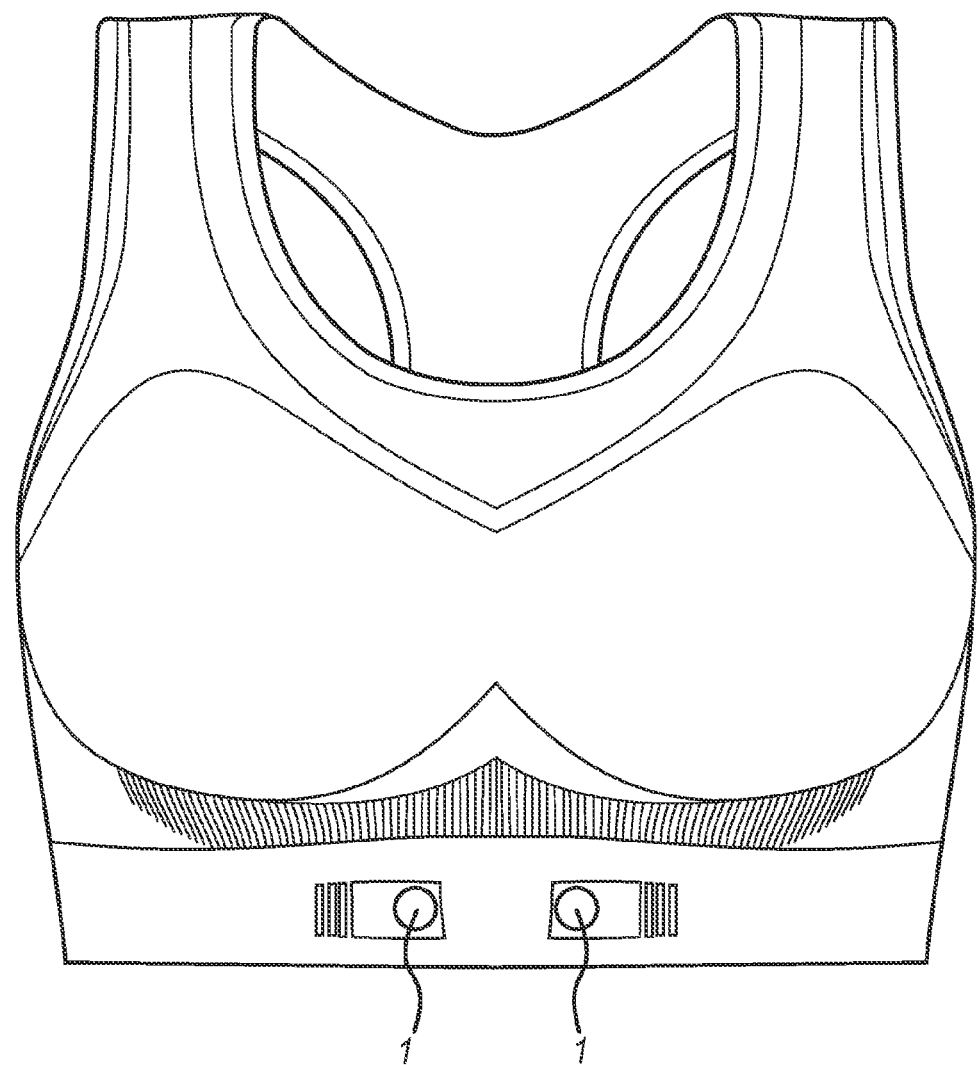

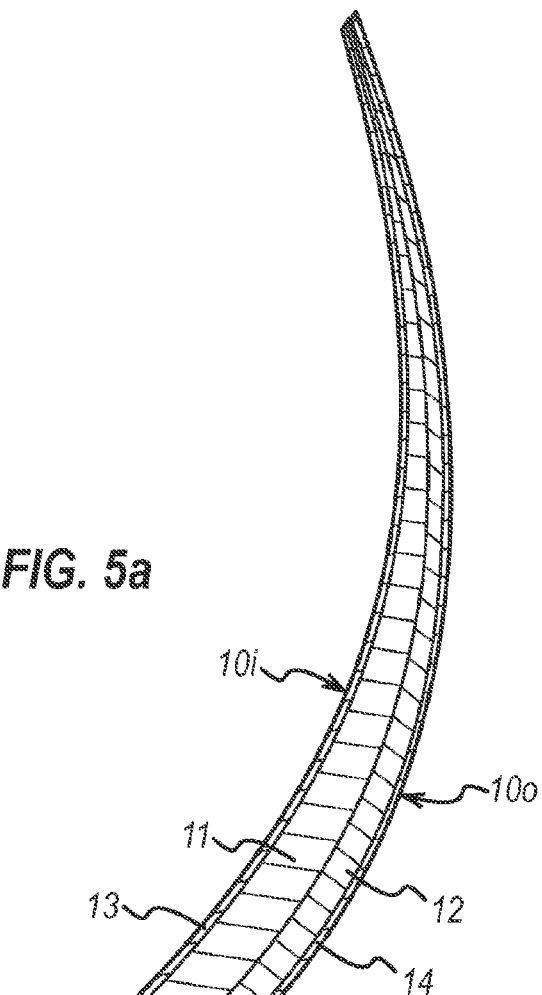
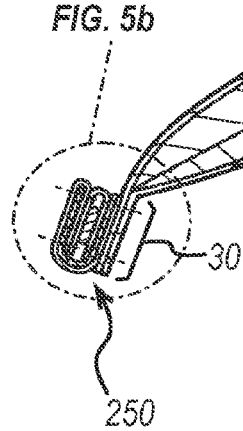
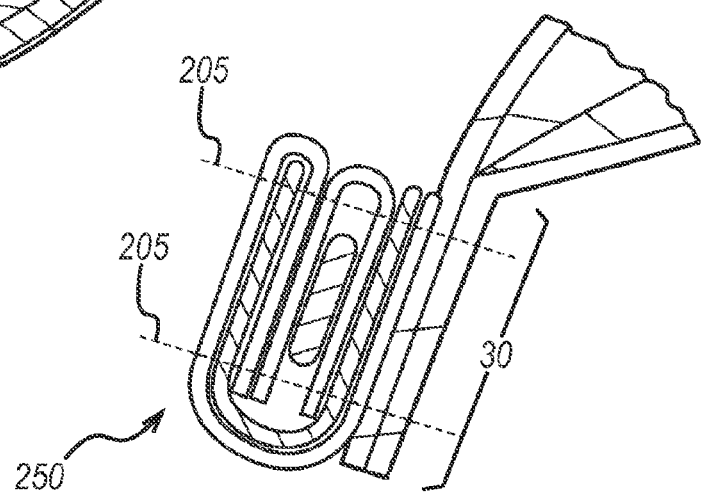
FIG. 5a
FIG. 5b

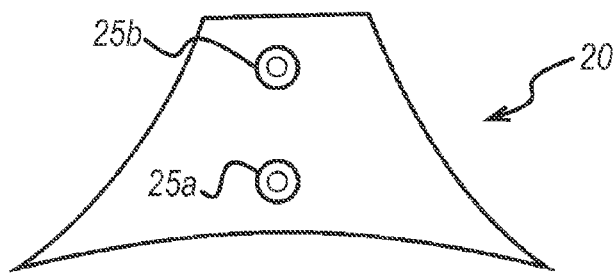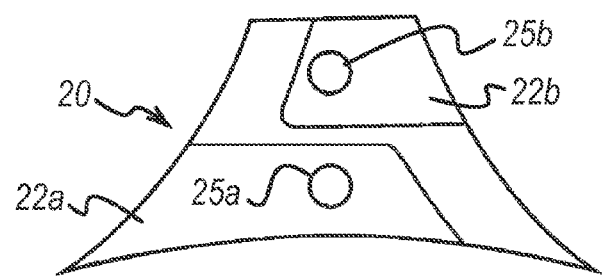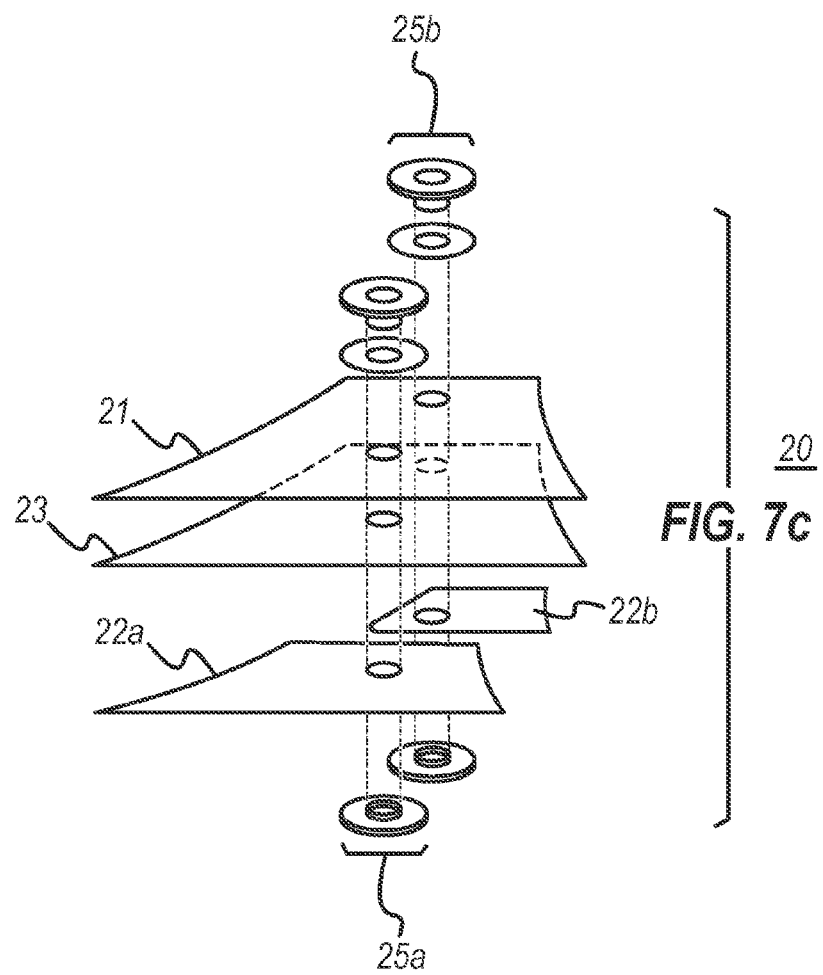

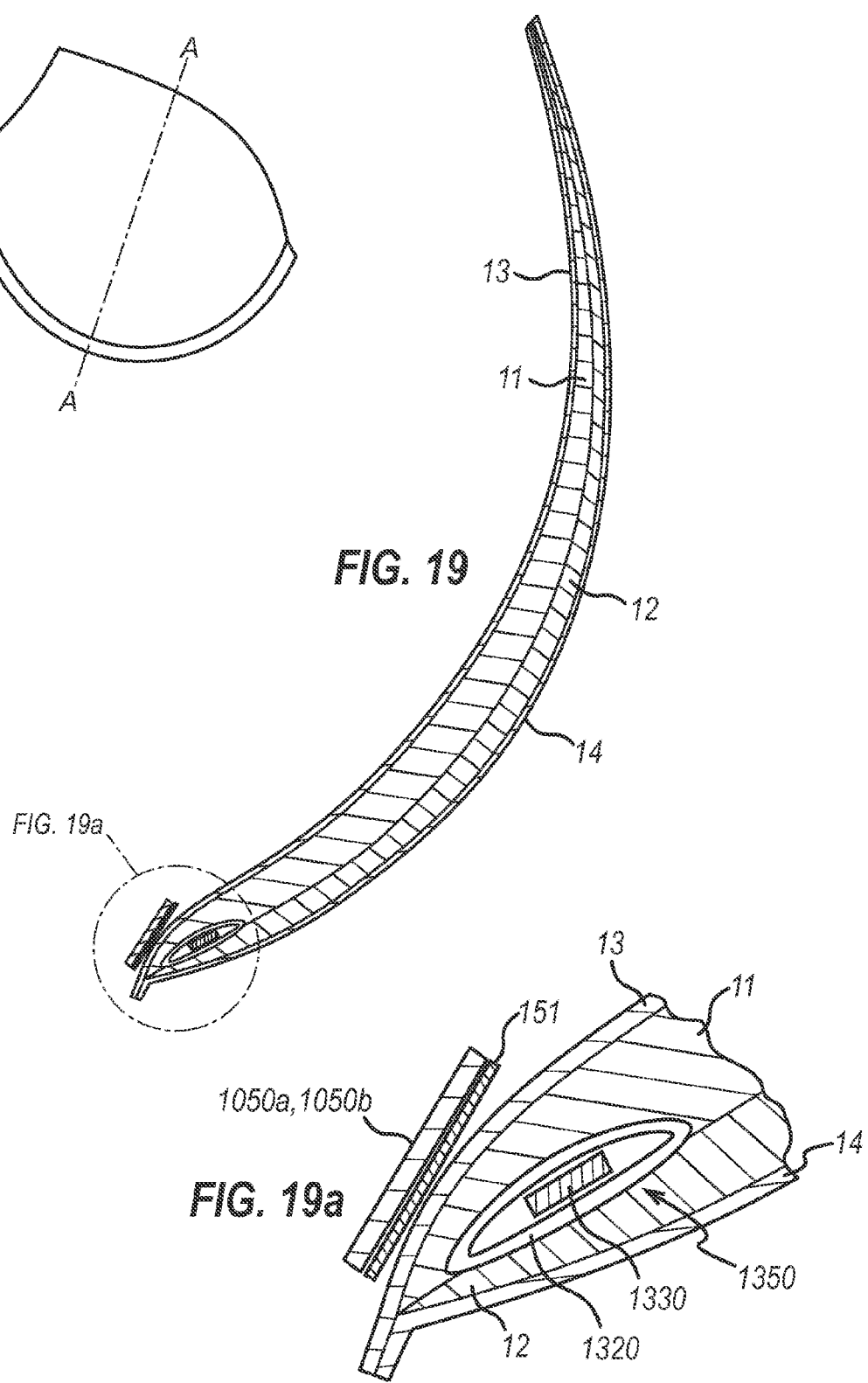

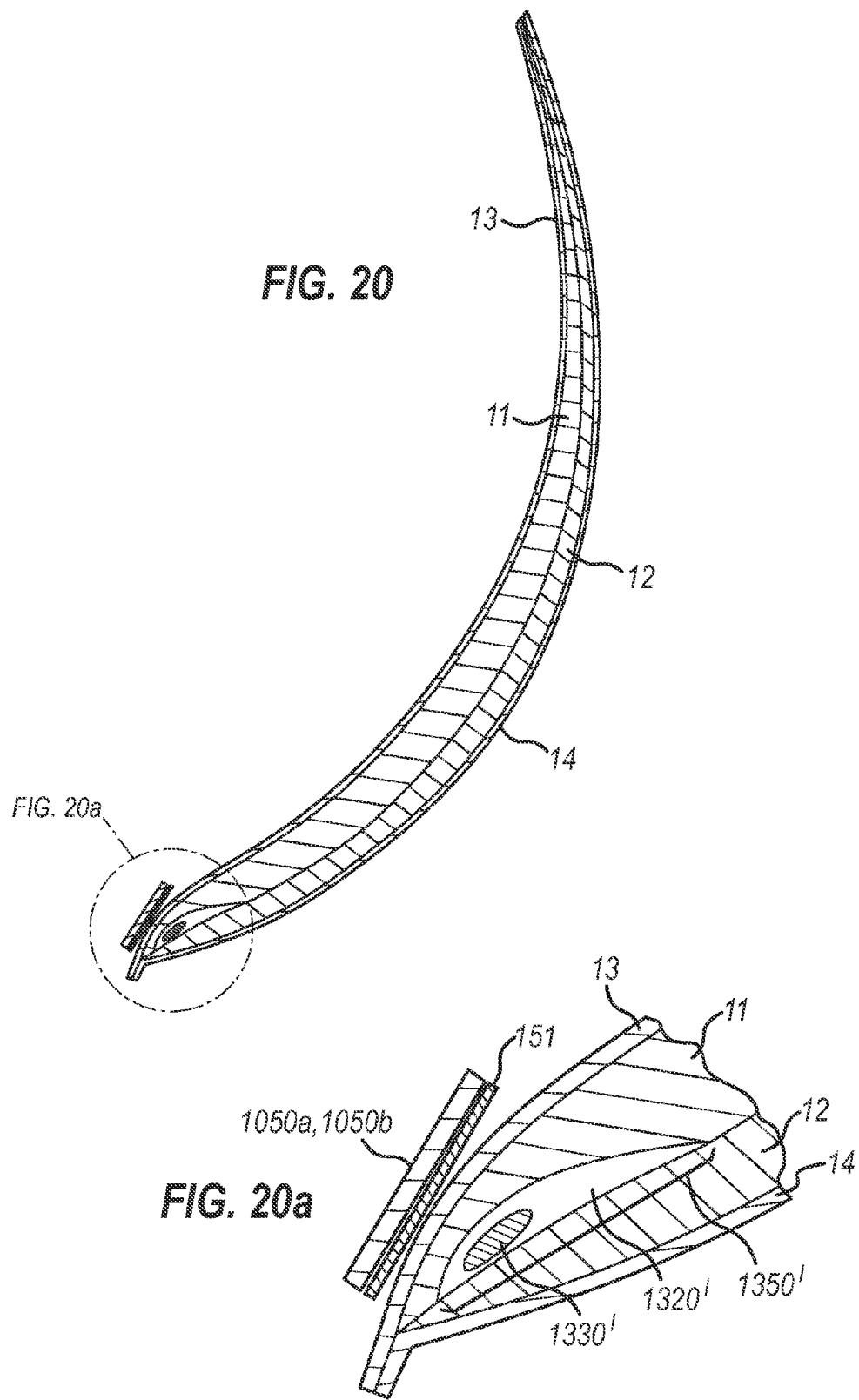

BRA AND BRA COMPONENTS

CROSS-REFERENCE TO RELATED APPLICATIONS

This application claims priority to and the benefit of Chinese Patent Application No. 201510032889.6, filed on 22 Jan. 2015, and of PCT International Patent Application No. PCT/CN2014/000532, filed on 26 May 2014; the disclosures of these documents are incorporated herein by reference in their entirety.

FIELD OF THE INVENTION

The present invention relates in general to a bra which has a built-in mechanism to enable monitoring of, for example, the wearer's heart rate. The present invention also relates to the components of the bra which enable it to achieve its monitoring function.

BACKGROUND

There is a growing demand for equipment that enables an individual to monitor their own heart rate, for example when exercising to ensure they are exercising at the optimum heart rate.

Chest heart rate monitors usually comprise two electrical sensors, a chest transmitter and a receiving device, e.g. a sports watch, a smart phone or cardio equipment. The electrical sensors of the heart rate monitor pick up the electrical activity of the heart and transmit the signals to the transmitter.

Chest heart rate monitors have been incorporated into sports bras. Sports bras are usually designed to be put on by being pulled over the head, with or without additional fastening means. The bras have cup regions to support the breasts and a chest band below the cup regions to maintain the positioning of the bra on the user. Sports bras have been developed which comprise a conductive fabric on the inner surface of the chest band to transmit a wearer's heart rate to a transmitter located within or on the chest band.

One example of such a prior art sports bra is the "miCoach Seamless Sports Bra" by Adidas®, which is illustrated in FIG. 1. Sensor fibers are knit into the fabric of the chest band on the inside (chest-facing side) to pick up the heart rate signals of the wearer. The chest band comprises a pocket (not shown) within the chest band at the front of the bra (accessible from the inner surface of the bra). The chest band further comprises transmitter fastening means in the form of snap buttons 1 passing through the chest band from the front surface of the chest band into the pocket to snappily receive a small transmitter that may be placed within the pocket. Heart rate signals are routed through the conducting fabric to the transmitter.

Sports bras are generally provided in four sizes (e.g. small, medium, large, extra-large), dependent on chest size. Each size can span a number of cup sizes. The position of the bra relative to the wearer's body may change with movement of the wearer as the bra is not always well fitted due to the fact that there are only four size options. The movement of the bra increases the risk of losing the heart rate signal. Furthermore, females tend to wear sports bras for exercise only, exchanging them for everyday conventional bras afterwards, for example for aesthetic or comfort reasons.

It is an object of the present invention to provide a bra for monitoring the heart rate of the wearer which may enhance the picking up of the heart rate signal and reduce the loss of the signal.

It would also be desirable to provide a bra that enables a user to monitor their heart rate during daily activities when a normal (none sport-specific) bra is worn.

SUMMARY OF THE INVENTION

In a first aspect of the present invention, there is provided an underwire casing for a bra, the underwire casing comprising an electrically conductive fabric layer.

In a first embodiment, the underwire casing comprises a fabric casing for receiving an underwire and the electrically conductive fabric layer is wrapped around the fabric casing. The underwire casing may comprise a further electrically conductive fabric layer within the fabric casing for receiving an underwire.

In a second embodiment, the electrically conductive fabric layer is formed into a tube for receiving an underwire.

In a second aspect of the present invention, there is provided a breast cup for a bra. The breast cup has an inner surface which is in contact with a wearer's body when worn, and an outer surface which faces away from the wearer's body when worn, and a lower edge region which is shaped to follow the shape of a wearer's breast and shaped to be positioned below a wearer's breast to support the breast. The lower edge region comprises an electrically conductive fabric layer on the inner surface for contact with the user's skin.

The breast cup may further comprise an underwire casing attached to the inner surface of the lower edge region, wherein the underwire casing comprises the electrically conductive fabric layer for contact with the user's skin.

In one embodiment, the underwire casing comprises a fabric casing for receiving an underwire and the electrically conductive fabric layer wrapped around the fabric casing. The electrically conductive fabric layer may wrap around the fabric casing and the underwire. The underwire casing may comprise a further electrically conductive fabric layer within the fabric casing for receiving an underwire.

In another embodiment, the electrically conductive fabric layer is formed into a tube for receiving an underwire.

In a third aspect of the present invention, there is provided a bra having an inner surface which is in contact with a wearer's body when worn, and an outer surface which faces away from the wearer's body when worn. The bra comprises: a left breast cup; a right breast cup; and a center gore attached between the left and right breast cups. Each of the left and right breast cups comprises a lower edge region which is shaped to follow the shape of a wearer's breast and is shaped to be positioned below a wearer's breast to support the breast, and wherein the lower edge region comprises an electrically conductive fabric layer on the inner surface for contact with the user's skin. The center gore comprises an attachment area for attachment of a transmitter and an electrically conductive pathway from the electrically conductive fabric of the lower regions of the breast cups to the attachment area.

The center gore preferably comprises an outer layer and an inner layer, wherein the electrically conductive pathway is positioned between the inner and outer layers. At least one of the inner and outer layers is preferably waterproof and/or electrically insulating. At least one of the inner and outer layers may be a fabric layer, a coating, or a film.

The center gore preferably comprises an electrically conductive fabric layer which forms the electrically conductive pathway from the electrically conductive fabric of the lower regions of the breast cups to the attachment area.

The electrically conductive fabric layer of the gore may be on the inner surface of the gore, in contact with the user's body when worn. Alternatively, the center gore may comprise an outer layer and an inner layer, and the electrically conductive fabric is positioned between the inner and outer layers. A portion of the electrically conductive fabric layer may extend beyond the inner layer and fold over the inner layer, such that the electrically conductive layer of the gore contacts the electrically conductive fabric layer of the lower edge region of the breast cups.

In a preferred embodiment, the center gore comprises a first attachment point and a second attachment point, wherein the electrically conductive fabric layer is in two portions, a first portion which passes from the electrically conductive fabric layer of the left breast cup to the first attachment point and a second portion which passes from the electrically conductive fabric layer of the right breast cup to the second attachment point. The first and second attachment points may comprise first and second holes through the center gore. The first and second attachment points may further comprise first and second conductive fasteners secured in the first and second holes for attaching to first and second portions of a transmitter. The first and second fasteners may comprise button fasteners for snappily receiving first and second portions of a transmitter or magnetic fasteners for magnetically receiving first and second portions of a transmitter.

The bra may further comprise at least one sidewing attached to and extending from at least one of the left and right bra cups. The at least one sidewing may comprise an electrically conductive fabric layer on at least a portion of the inner surface in contact with the wearer when the bra is worn.

Each breast cup may further comprise an underwire casing attached to the inner surface of the lower edge region, wherein the underwire casing comprises the electrically conductive fabric layer for contact with the user's skin.

In one embodiment, the underwire casing comprises a fabric casing for receiving an underwire and the electrically conductive fabric layer is wrapped around the fabric casing. The electrically conductive fabric layer may wrap around the fabric casing and the underwire. The underwire casing may comprise a further electrically conductive fabric layer within the fabric casing for receiving an underwire.

In a second embodiment, the electrically conductive fabric layer is formed into a tube for receiving an underwire.

The bra may further comprise an underwire positioned within the underwire casing of each breast cup.

In a fourth embodiment of the present invention, there is provided a center gore for attaching together two breast cups for a bra, the center gore comprising an attachment area for attaching a transmitter and a layer of electrically conductive fabric for transmitting an electrical signal to the attachment area. The center gore may comprise an outer layer and an inner layer, wherein the layer of electrically conductive fabric is positioned between the inner and outer layers. At least one of the inner and outer layers is preferably waterproof and/or electrically insulating. At least one of the inner and outer layers may be a fabric layer, a coating, or a film. A portion of the electrically conductive fabric layer may extend beyond the inner layer and folds over the inner layer.

The electrically conductive fabric layer of the gore is preferably on the inner surface of the gore, in contact with the wearer's body when worn.

BRIEF DESCRIPTION OF THE DRAWINGS

Preferred embodiments of the present invention will now be described with reference to the accompanying drawings, in which:

FIG. 1 shows a prior art sports bra which has attachment buttons for attachment to a transmitter placed within the chest band (not shown);

FIG. 3b shows a cross sectional view of the underwire casing (including an underwire) of FIG. 3a;

FIG. 4b shows a cross sectional view of the underwire casing (including an underwire) of FIG. 4a;

FIG. 5a shows a breast cup comprising the underwire casing of FIG. 3a in accordance with the present invention;

FIG. 5b is an enlarged portion of FIG. 5a, with sew lines illustrated;

FIG. 7a is a front view of the center gore shown in FIGS. 2a-c, in accordance with the present invention;

FIG. 7b is a back view of the center gore shown in FIGS. 2a-c, in accordance with the present invention;

FIG. 7c is an exploded view of the components of the center gore shown in FIGS. 7a and 7b;

FIG. 9b shows a cross sectional view of the underwire casing (including an underwire) of FIG. 9a;

FIG. 17b shows a back view of the bra shown in FIG. 17a;

FIG. 18 shows a bra cup with a line indicated for cross-sectional views;

FIG. 19 shows a cross-sectional view of a breast cup comprising a conductive fabric layer in accordance with the present invention;

FIG. 19a is an enlarged portion of FIG. 19, with adhesive illustrated;

FIG. 20 shows a cross-sectional view of a breast cup comprising a conductive fabric layer in accordance with the present invention; and FIG. 20a is an enlarged portion of FIG. 20, with adhesive illustrated.

DETAILED DESCRIPTION

The present invention will now be described with reference to FIGS. 2a-12b. The present invention relates to an alternative bra for monitoring a wearer's heart rate (or any other electrical signal of interest), and to components of that alternative bra that enable the monitoring.

Figure 2A:
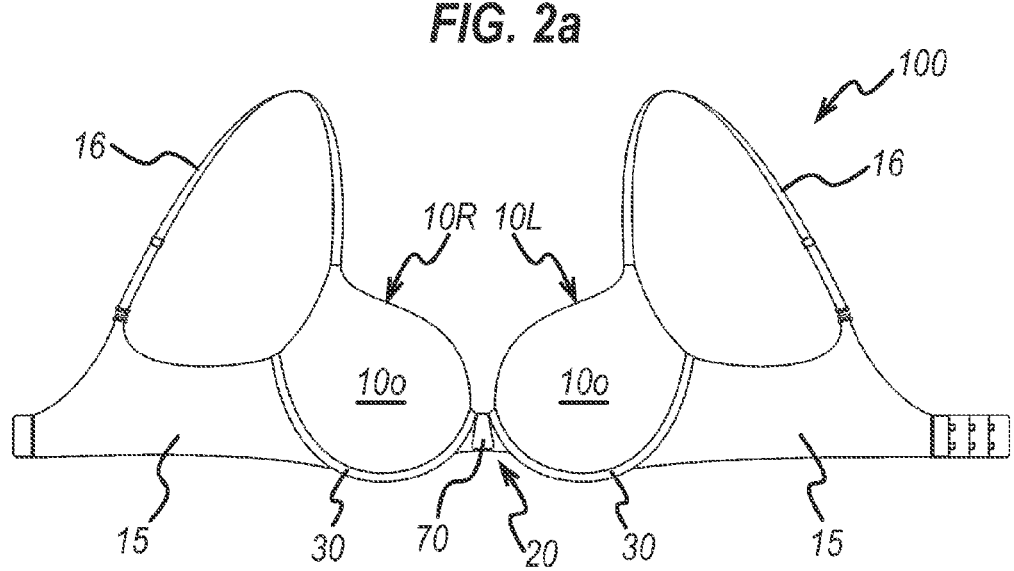
FIG. 2a shows a front view of a bra according to an embodiment of the present invention, with a transmitter attached to a center gore.
Figure 2B:
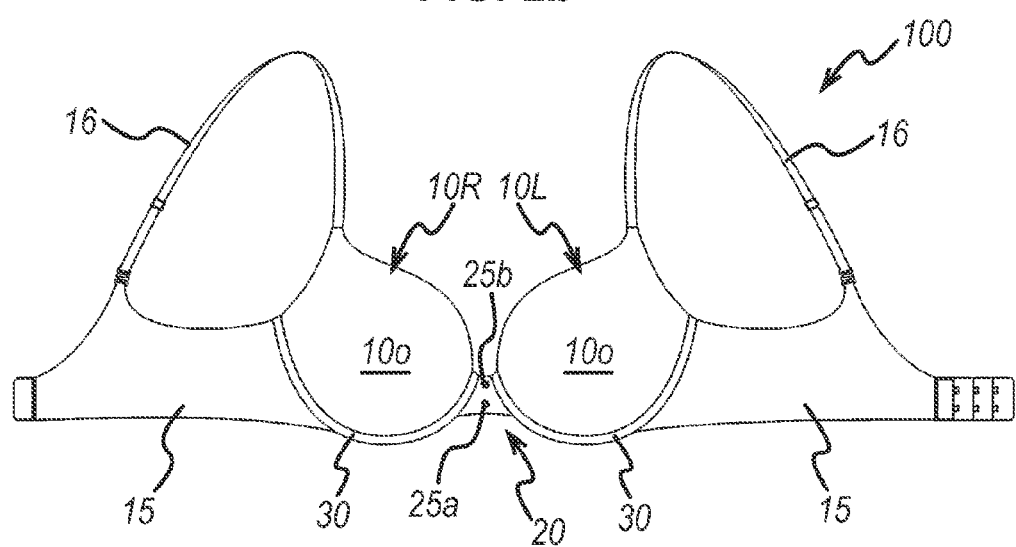
FIG. 2b shows a front view of the bra of FIG. 2a, without a transmitter.
Figure 2C:
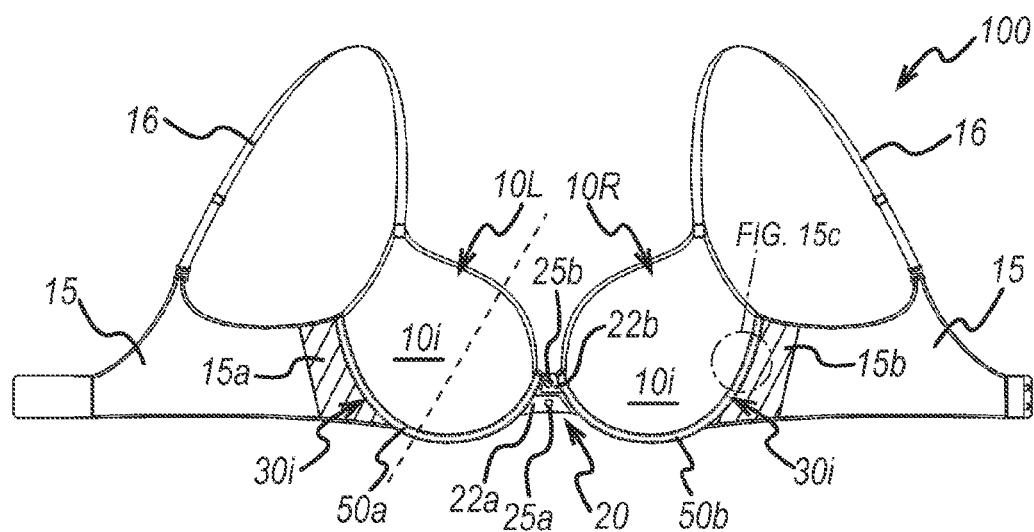
FIG. 2c shows a rear view of the bra of FIG. 2a or 2b.

FIGS. 2a-c illustrate a bra 100 in accordance with the present invention. The bra 100 is a conventional bra comprising a pair of breast cups 10L, 10R intended to support the breasts of the wearer, a connecting portion, or center gore 20, joining together the inner edges of the cups at the wearer's cleavage, and at least one strap or back wing 15 that extends from outer edges of the breast cups around the back of the wearer. The bra 100 may further include shoulder straps 16 that extend from upper edges of the breast cups over the shoulders of the wearer to attachment points on the back wing 15 crossing the wearer's back.

Each breast cup 10L, 10R has an inner surface 10i (shown in FIG. 2c) which is in contact with a wearer's body when worn and an outer surface 10o (shown in FIGS. 2a and 2b) which faces away from the wearer's body when worn. Referring to FIG. 2b, each breast cup 10L, 10R further comprises a lower edge region 30 which is shaped to follow the shape of a wearer's breast and is shaped to be positioned below a wearer's breast to support the breast when worn. The lower edge region 30 comprises an inner surface 30i which faces the wearer's body when the bra is worn.

The bra 100 in accordance with the present invention may be underwired. An underwire bra comprises an underwire for each breast cup to shape and support the lower periphery of each breast cup. The underwire comprises a generally U-shaped frame formed from metal or a rigid plastic material.

With reference to FIG. 2c, a first embodiment of a bra 100 according to the present invention is an underwired bra 100 having underwire casings 50a, 50b attached to the inner surface 30i of the lower edge regions 30 of the breast cups. The underwire casings 50a, 50b house underwires (not shown in FIG. 2c).

The underwire casings 50a, 50b comprise an electrically conductive fabric layer in contact with the wearer's skin to pick up electrical heart activity and transmit the electrical signals through the electrically-conductive fabric to the center gore 20, attachment points 25a, 25b of the gore 20, and transmitter 70 (as shown in FIG. 2a).

As shown in the embodiment as illustrated in FIG. 2c, FIGS. 7a-7c and FIGS. 8a-8b, the center gore 20 comprises two electrically conductive attachment points 25a, 25b (described in more detail later) for attachment of a transmitter, and two electrically conductive fabric portions 22a, 22b. The first electrically conductive fabric portion 22a is in contact with and/or extends from the electrically conductive fabric of the underwire casing 50a of the left breast cup 10L to the first attachment point 25a. Similarly, the second electrically conductive fabric portion 22b is in contact with and/or extends from the electrically conductive fabric of the underwire casing 50b of the right breast cup 10R to the second attachment point 25b.

Thus, any electrical signals picked up by the electrically conductive fabric of the underwire casings 50a, 50b is passed through the electrically conductive fabric of the casings 50a, 50b, through the electrically conductive fabric portions 22a, 22b of the center gore 20, and to the attachment points 25a, 25b for the transmitter. The electrically conductive attachment points 25a, 25b (which will be described in more detail later) then transmit the electrical signal to the transmitter 70 (when attached, as shown in FIG. 2a) for transmission of the electrical signal to a receiver (not shown).

Figure 15A:
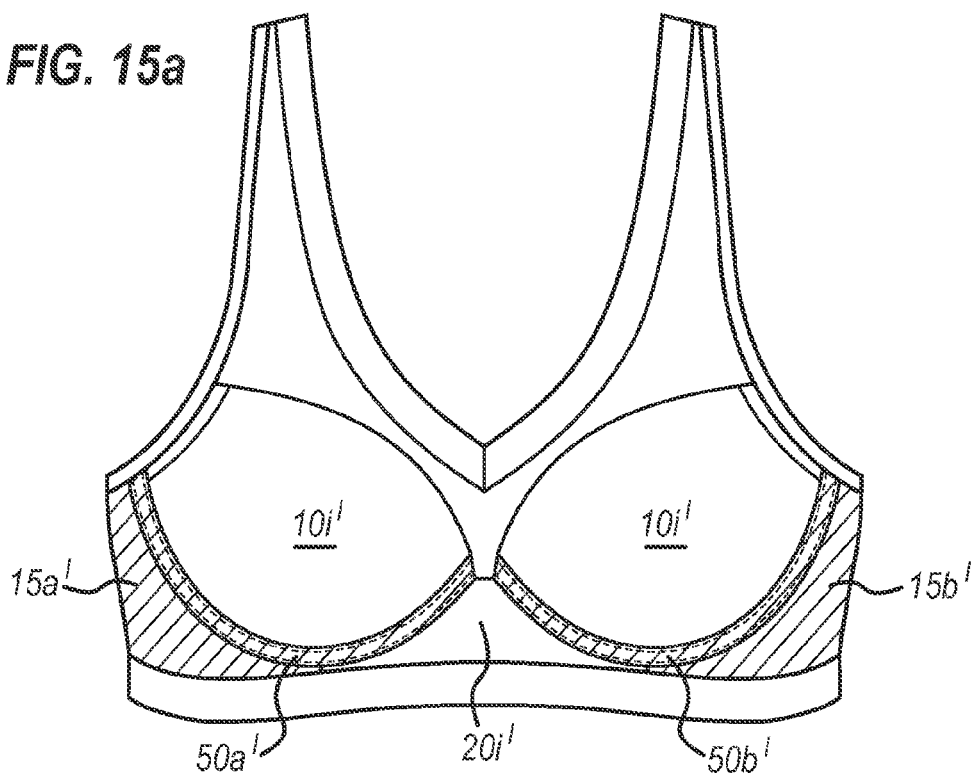
FIG. 15a shows an alternative back view of the bra shown in FIG. 13.
Figure 15B:
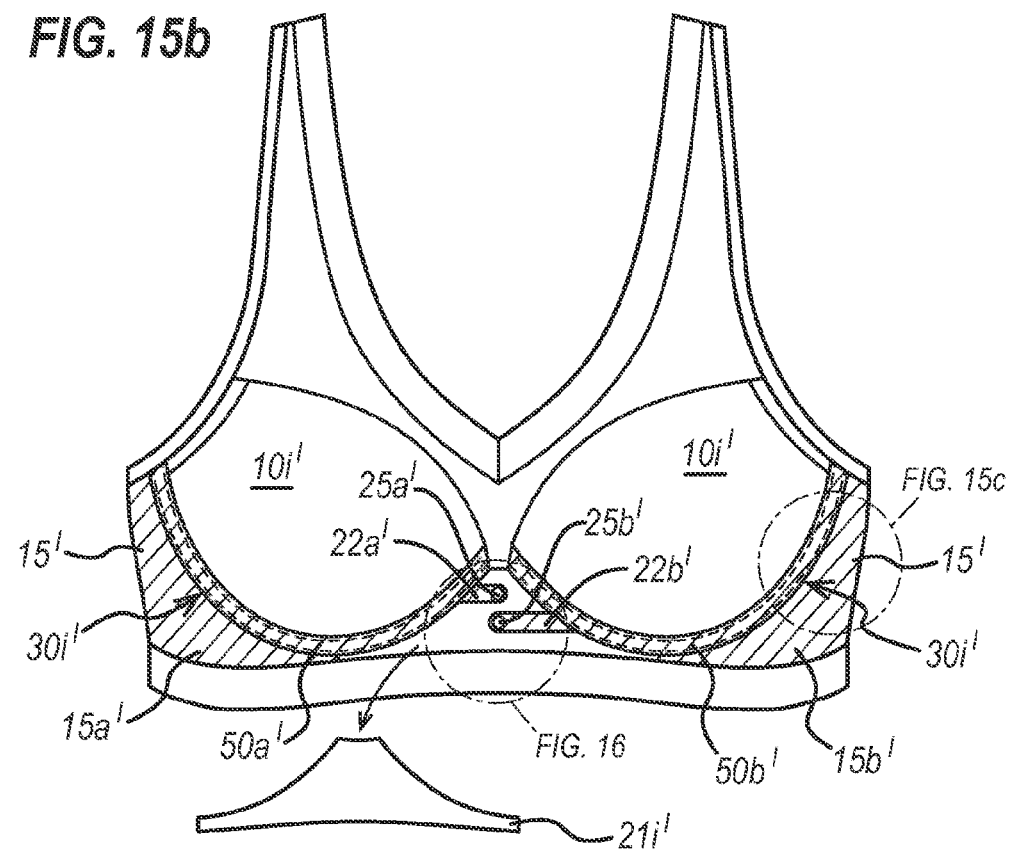
FIG. 15b shows the back view of FIG. 15a, with an inner layer of the center gore removed to show the conductive fabric layer of the center gore.
Figure 15C:
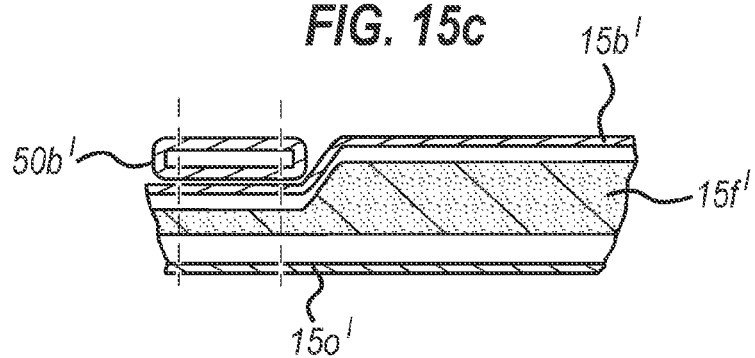
FIG. 15c is a cross section showing a layer structure at the underwire and sidewing region.

As shown in FIG. 2c, the sidewings 15 optionally comprise, on an inner surface, electrically conductive fabric portions 15a, 15b at the regions where the sidewings 15 attach to the breast cups 10i. The electrically conductive fabric portions 15a, 15b of the sidewings 15 therefore extend the electrical pathway, such that the pathway passes through the electrically conductive sidewing portions 15a, 15b, casings 50*a*, 50*b*, gore 20 and attachments 25*a*, 25*b*. The electrically conductive portions 15*a*, 15*b* of the sidewings 15 may enhance signal pickup through increased contact area under firm pressure. The sidewings 15 may comprise a foam layer at the conductive portions 15*a*, 15*b* to increase the pressure against the user's body at this region, thus enhancing signal pickup. A cross-sectional view of the layers of the sidewing 15' is illustrated in FIG. 15*c*, and is described with reference to that figure later.

FIG. 2*a* shows the transmitter 70 attached to the attachment points 25*a*, 25*b* of the bra 100. The transmitter 70 is detachable and is preferably removed from the bra 100 (as shown in FIG. 2*b*) when it is not needed or when the bra 100 is being washed.

The bra 100 of the first embodiment of the present invention therefore uses the underwire casings 50*a*, 50*b* to sense and transmit electrical heart signals to the transmitter 20 (via the central gore 20). The location of the underwire casing 50*a*, 50*b*, on the inner surface 30*i* of the lower edge regions 30 of the breast cups 10L, 10R, is a good location to pick up the heart rate signals, because the underwire casings 50*a*, 50*b* are firmly pressed against the wearer's skin at the appropriate location. The underwire casings 50*a*, 50*b* of the bra comprise underwires. The underwire assemblies (casings including underwires) are relatively fixed relative to the wearer's body as they provide their supportive function, positioned under the wearer's breasts. Furthermore, because conventional bras have various cup sizes in addition to dimensional sizes, the underwire casings 50*a*, 50*b* usually fit the wearer's body well, enhancing the signal pick up.

The present invention also relates to underwire casings 50*a*, 50*b* comprising an electrically conductive fabric layer. Preferred embodiments of the underwire casings 50*a*, 50*b* of FIGS. 2*a-c* will now be described in more detail with reference to FIGS. 3*a*-6*b* and FIGS. 9*a*-10*b*.

Figure 3A:
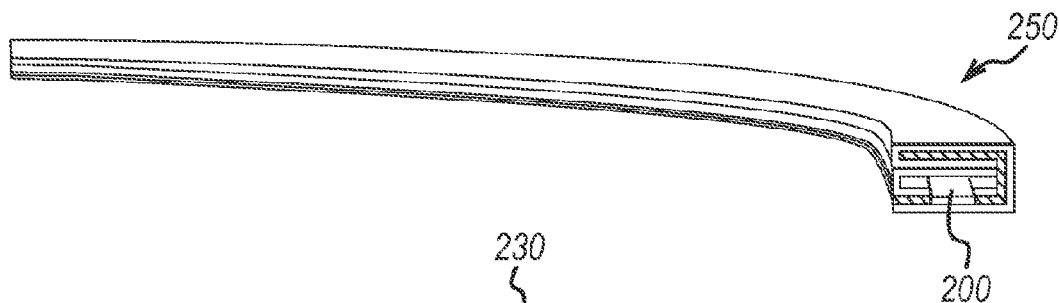
FIG. 3a shows an underwire casing (including an underwire) in accordance with a first embodiment of the present invention.
Figure 3B:
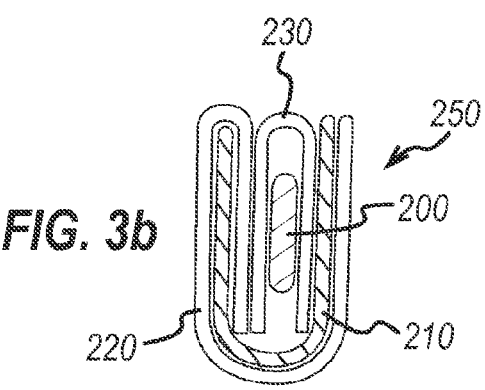

FIGS. 3*a* and 3*b* illustrate a first embodiment of an underwire casing 250 in accordance with the present invention. FIG. 3*a* shows an end-on perspective view of the underwire casing 250 and FIG. 3*b* shows a cross-section of the underwire casing 250 shown in FIG. 3*a*. The underwire casing 250 comprises a normal fabric (i.e. non-electrically conductive) casing 210 for surrounding an underwire 200. The underwire casing 250 further comprises an electrically conductive fabric layer 220 that is wrapped around the fabric casing 210 housing the underwire 200. As illustrated, the edge of the electrically conductive fabric layer 220 is preferably folded into the center of a U-shaped fabric casing 210, with the underwire 200 being positioned between the folded-in edge of the conductive fabric layer 220 and the fabric casing 210. By folding-in the outer conductive layer 220 in this manner, the underwire can also function to transmit electrical signals, if that underwire is electrically conducting (e.g. made from metal). In a preferred variation of this embodiment (shown in FIGS. 3*a* and 3*b*), an additional U-shaped layer of electrically conducting fabric 230 is wrapped around the underwire 200, within the normal fabric casing 210. This additional electrically conductive fabric layer 230 serves to cover and prevent exposure of the underwire 200, and also to enhance the conducting path provided by the electrically conductive fabric 220 that wraps around the fabric casing 210. This additional electrically conductive fabric layer 230 also acts as a "backup" in case the outer electrically conductive fabric layer 220 is damaged or otherwise not functioning. In another preferred variation of this embodiment (shown in FIGS. 9*a* and 9*b*), the underwire casing 950 comprises an electrically conductive fabric layer 920 that is wrapped around a normal (i.e. non-electrically conductive) fabric casing 910 and the underwire 900. In this variation, a single piece of electrically conductive fabric 920 is used to wrap around the underwire casing 950 and the underwire 900, thereby saving production cost.

Figure 4A:
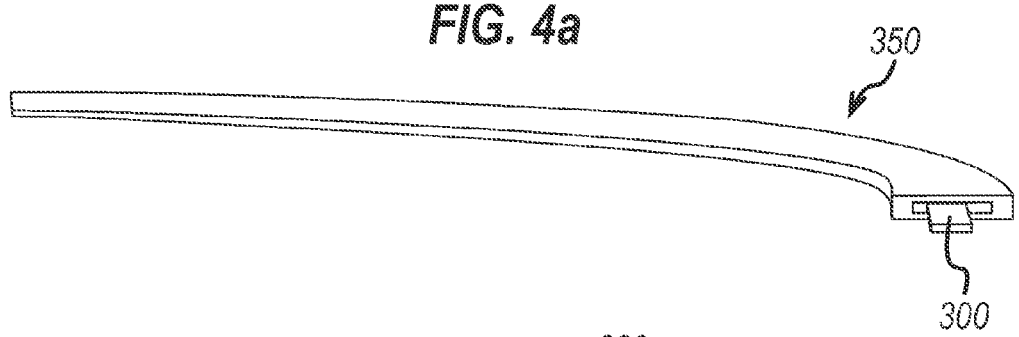
FIG. 4a shows an underwire casing (including an underwire) in accordance with a second embodiment of the present invention.
Figure 4B:
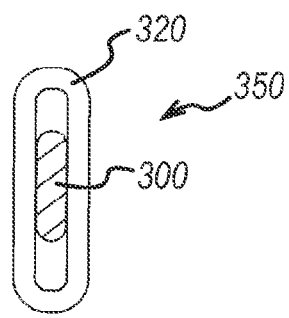

FIGS. 4*a* and 4*b* illustrate a second embodiment of an underwire casing 350 in accordance with the invention. FIG. 4*a* shows an end-on perspective view of the underwire casing 350 and FIG. 4*b* shows a cross-section of the underwire casing 350 shown in FIG. 4*a*. The underwire casing 350 is formed from an electrically conductive fabric layer 320 which surrounds an underwire 300. The underwire casing may be formed from a tube (as illustrated) of electrically conductive fabric 320 or may be formed from a U-shaped fabric layer 320 which is sewn along the open edge to provide a tube.

FIGS. 5*a*, 5*b*, 6*a*, 6*b*, 10*a* and 10*b* illustrate the attachment of the underwire casings of the first 250, 950 and second 350 embodiments to a breast cup of a bra, for example the breast cup 10L, 10R of the bra 100 illustrated in FIGS. 2*a-c*. FIGS. 5*a*, 5*b*, 6*a*, 6*b*, 10*a* and 10*b* are cross-sectional views of a breast cup 10L, 10R taken along the dotted line shown in FIG. 2*c*.

In particular, FIGS. 5*a* and 5*b* illustrate the attachment of the underwire casing 250 of FIGS. 3*a* and 3*b* to an inner surface 30*i* of the lower edge region 30 of a breast cup 10L, 10R. As shown by sew lines 205, a preferred means of attaching the underwire casing to the breast cup is to sew along the length of the upper and lower edges of an underwire casing 250 that is positioned on the inner surface 30*i* of the lower edge region 30 of a breast cup 10L, 10R (as also shown by the sew lines in FIGS. 2*c*, 8*a* and 8*b*), the sewing threads passing through all of the layers of the underwire casing and the lower region 30 of the breast cup 10L, 10R. The sew threads can therefore secure the layers of the underwire casing 250 together as well as securing the underwire casing 250 to the lower edge region 30 of the breast cup 10L, 10R.

Figure 8A:
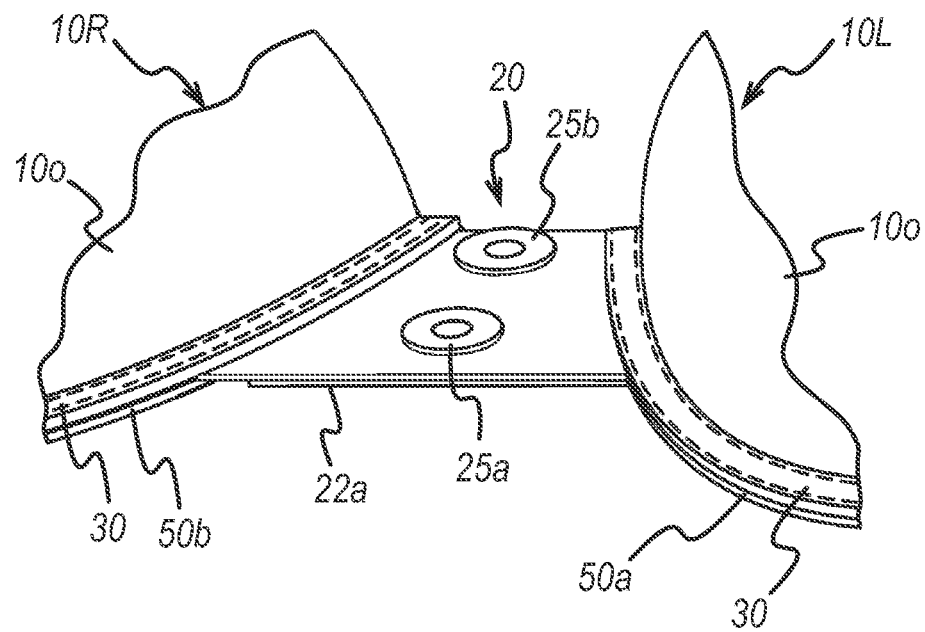
FIG. 8a is a front perspective view (taken from below) of the bra of FIGS. 2a-c showing the center gore attached to the breast cups, in accordance with the present invention.
Figure 8B:
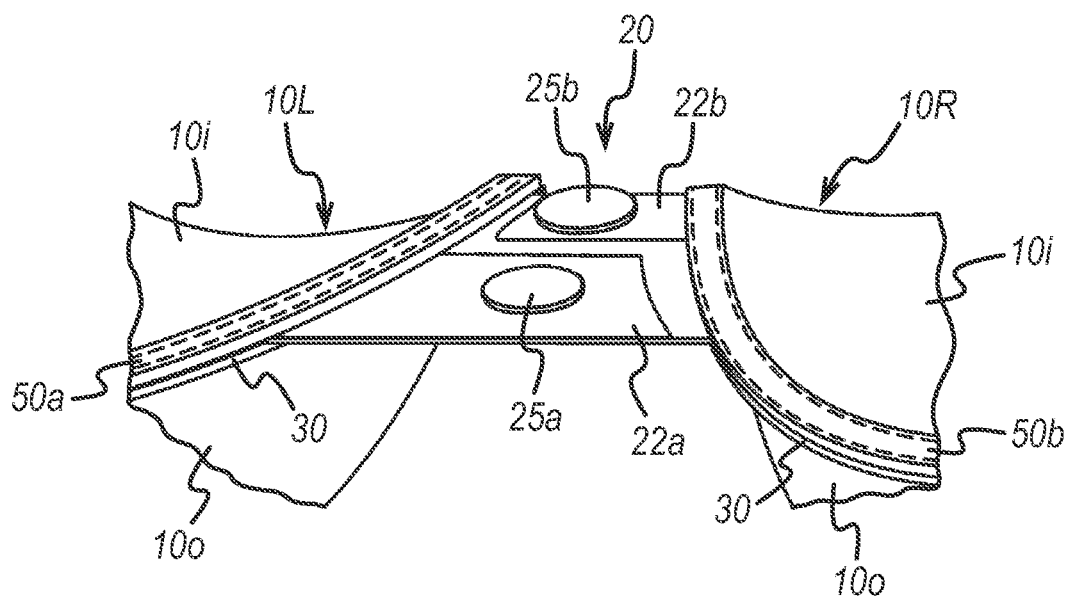
FIG. 8b is a back perspective view (taken from above) of the bra of FIGS. 2a-c showing the center gore attached between the breast cups and underwire casings, in accordance with the present invention.
Figure 9A:
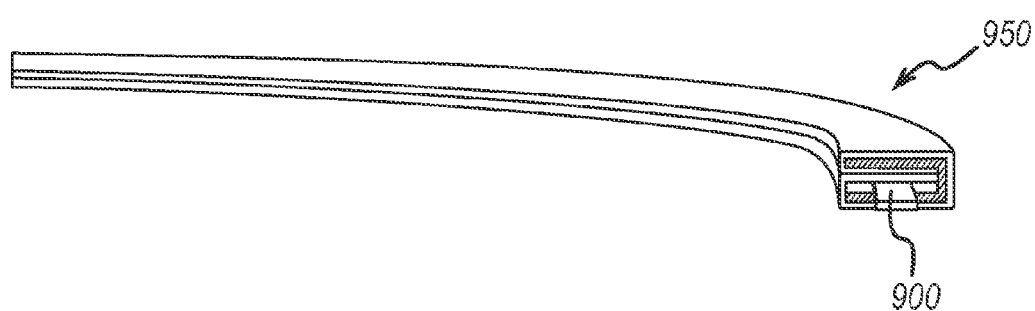
FIG. 9a shows an underwire casing (including an underwire) in accordance with an alternative embodiment of the present invention.
Figure 9B:
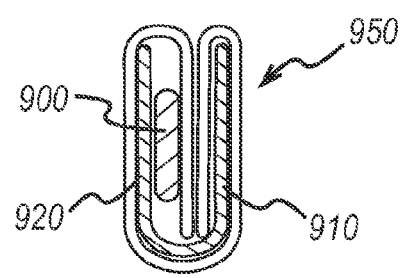
Figure 10A:
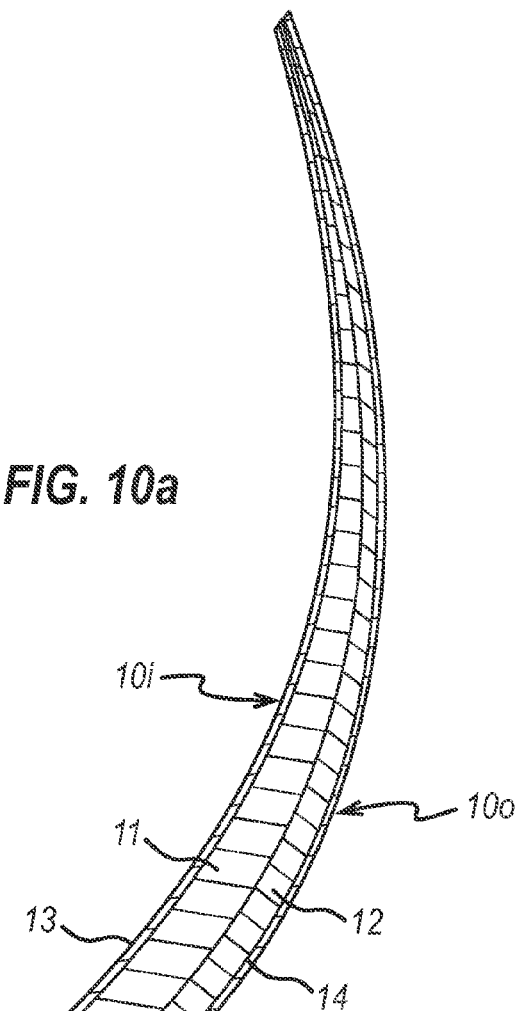
FIG. 10a shows a breast cup comprising the underwire casing of FIG. 9a in accordance with the present invention.
Figure 10B:
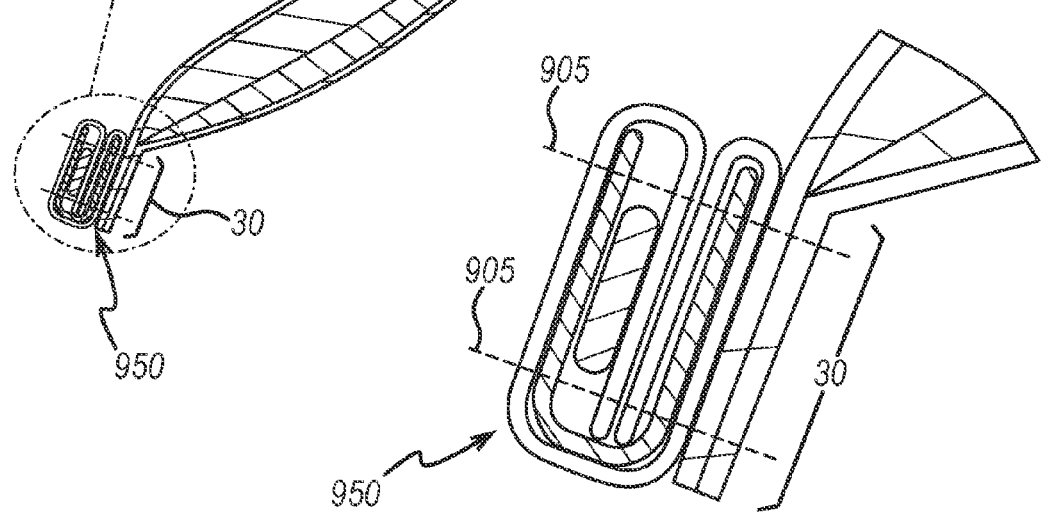
FIG. 10b is an enlarged portion of FIG. 10a, with sew lines illustrated.

Similarly, FIGS. 10*a* and 10*b* illustrate the attachment of the underwire casing 950 of FIGS. 9*a* and 9*b* to an inner surface 30*i* of the lower edge region 30 of a breast cup 10L, 10R. As shown by sew lines 905, a preferred means of attaching the underwire casing to the breast cup is to sew along the length of the upper and lower edges of an underwire casing 950 that is positioned on the inner surface 30*i* of the lower edge region 30 of a breast cup 10L, 10R (as also shown by the sew lines in FIGS. 2*c*, 8*a* and 8*b*), the sewing threads passing through all of the layers of the underwire casing and the lower region 30 of the breast cup 10L, 10R. The sew threads can therefore secure the layers of the underwire casing 950 together as well as securing the underwire casing 950 to the lower edge region 30 of the breast cup 10L, 10R.

Figure 6A:
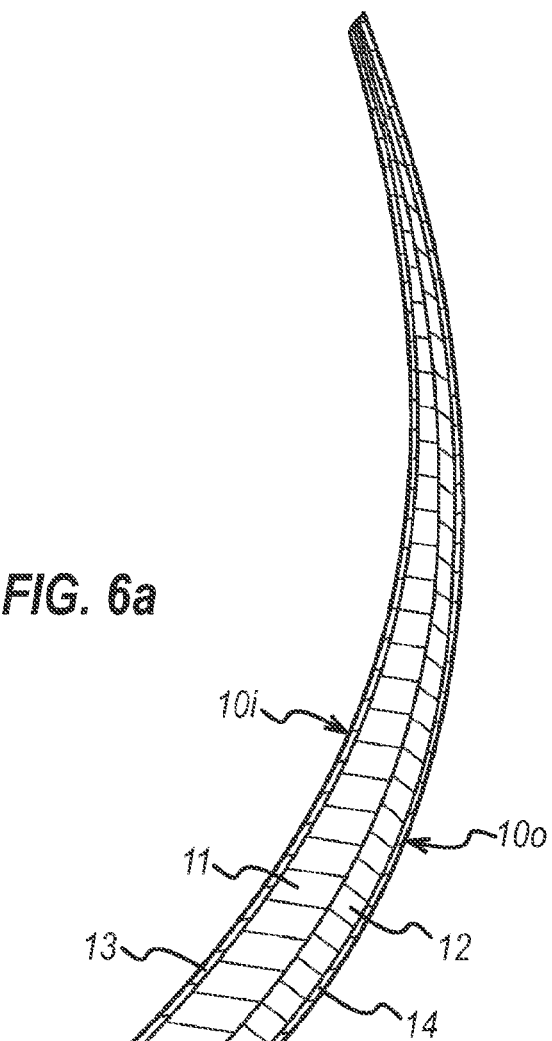
FIG. 6a shows a breast cup comprising the underwire casing of FIG. 4a in accordance with the present invention.
Figure 6B:
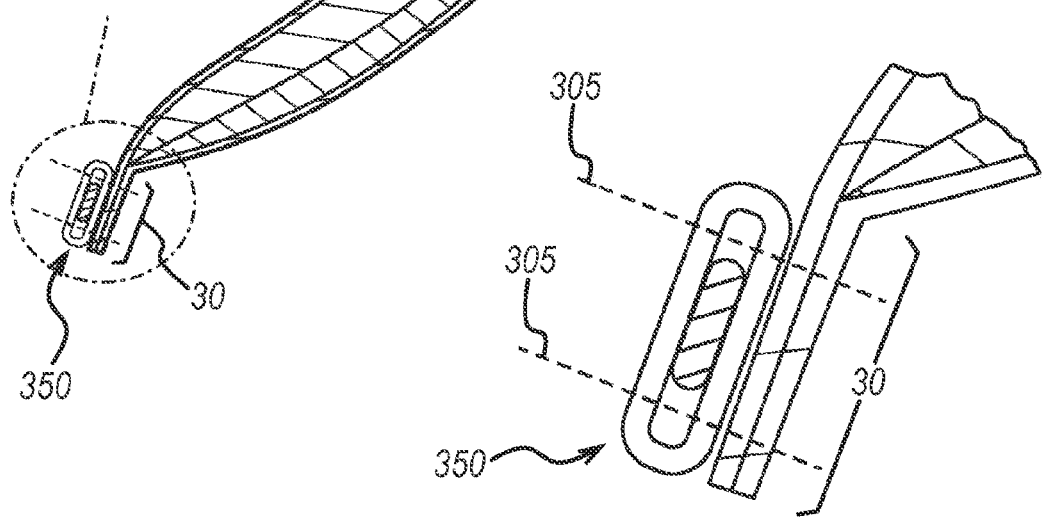
FIG. 6b is an enlarged portion of FIG. 6a, with sew lines illustrated.

Similarly, FIGS. 6*a* and 6*b* illustrate the attachment of the underwire casing 350 of FIGS. 4*a* and 4*b* to an inner surface 30*i* of the lower edge region 30 of a breast cup 10L, 10R. As shown by sew lines 305, a preferred means of attaching the underwire casing 350 to the breast cup is to sew along the length of the upper and lower edges of an underwire casing 350 that is positioned on the inner surface 30*i* of the lower edge region 30 of a breast cup 10L, 10R (as also shown by the sew lines in FIGS. 2*c*, 8*a* and 8*b*), the sewing threads passing through the layers of the underwire casing and the lower region 30 of the breast cup 10L, 10R.

As shown in FIGS. 5*a*-6*b* and FIGS. 10*a*-10*b*, the breast cup may be formed of an inner foam layer 11, an outer foam layer 12, an inner fabric layer 13 and an outer fabric layer 14. The inner 13 and outer 14 fabric layers form the lower edge region 30 of the breast cup 10L, 10R (with or without one or more of the foam layers therebetween). However, the bra of the present invention is not intended to be limited to the illustrated breast cup structure, which is shown for illustrative purposes. For example, any number of foam layers and/or fabric layers can be provided, and the breast cup may omit the foam layers altogether.

As will be understood from the above description, the underwire casings 250, 350 and 950 illustrated in FIGS. 3a-6b and FIGS. 9a-10b are preferred embodiments of those labelled 50a, 50b in FIGS. 2a-c and 8a-b.

Figure 16:
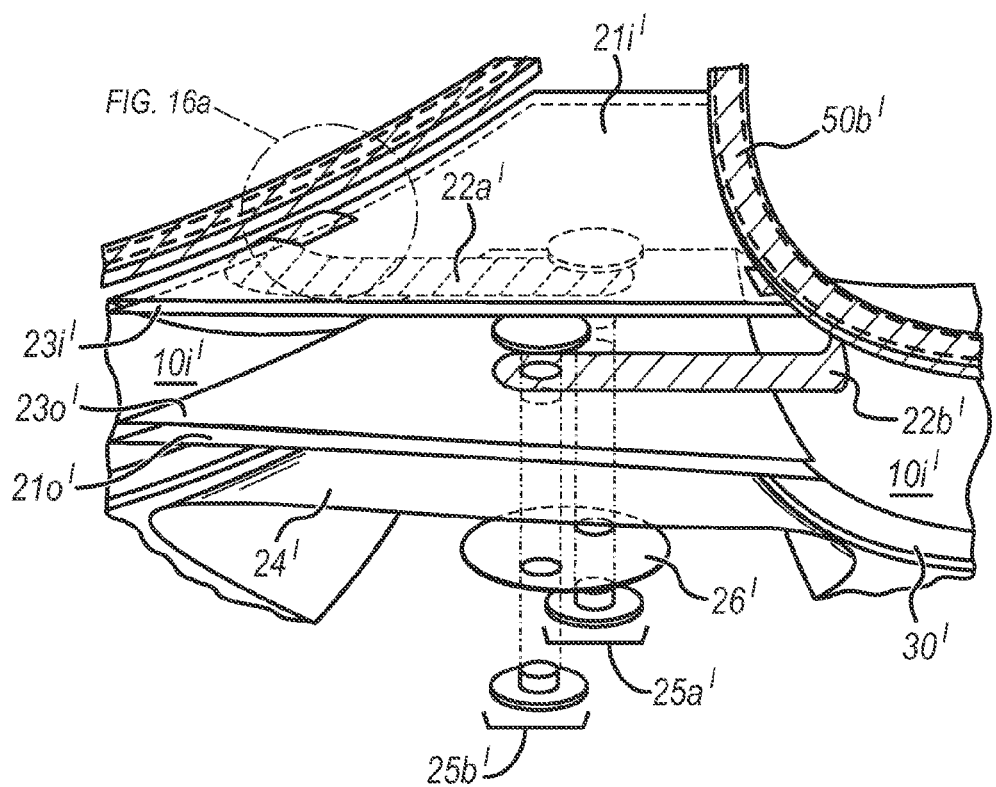
FIG. 16 is a front perspective exploded view (as indicated in FIGS. 14b and 15b) of the bra of FIGS. 14a-b and 15a-b, showing the center gore components, the underwire casings and the breast cups, in accordance with the present invention.

An embodiment of the center gore 20 of the present invention is illustrated in greater detail in FIGS. 7a-7c. 7a shows the outer surface (surface facing away from the wearer) of the center gore 20 (as seen in FIG. 2b) and FIG. 7b shows the inner surface (surface facing the user's body) of the center gore 20 (as illustrated in FIG. 2c). As shown in FIG. 7a, the attachment points 25a, 25b for a transmitter 70 are preferably button type fasteners, each of which comprises a recess (denoted by an inner circle) on the upper or the outer side of the center gore 20 for snappily receiving a corresponding protrusion of the transmitter. Thus, protrusions of the transmitter snap-fit into the recesses of the button type fasteners on the front center gore 20, attaching the transmitter 70 to the bra 100 (as shown in FIG. 2a). Other attachment points 25a', 25b' are possible, for example, magnetic connectors, as shown in FIGS. 16 and 17d.

As previously described (and as shown in FIG. 7b), the inner surface of the center gore 20 comprises a first electrically conducting fabric portion 22a to transmit an electrical signal from the underwire casing 50a of the left breast cup 10L to the first attachment point or button type fastener 25a, and a second electrically conducting fabric portion 22b to transmit an electrical signal from the underwire casing 50b of the right bra cup 10R to the second attachment point or button type fastener 25b. The attachment point or button type fasteners 25a, 25b are themselves electrically conductive (e.g. by virtue of being metallic) to allow transmission of an electric signal from the electrically conductive fabric portions 22a, 22b to the transmitter protrusions.

An exploded perspective view of the embodiment of the center gore as shown in FIGS. 7a and 7b is shown in FIG. 7c. Each button type fastener 25a, 25b preferably comprises a first component of a snap button, a washer/spacer, and a second component of the snap button. The snap button fasteners pass through holes in the fabric layers 21, 23, 22a, 22b of the center gore 20. In particular, the center gore comprises an upper fabric layer 21, which is preferably of the same fabric as the outer surface 10o of the breast cups 10L, 10R, a non-stretchable fabric layer 23, and the conductive fabric portions 22a, 22b. The non-stretchable fabric layer 23 prevents lateral movement of the two bra cups away from each other. An additional fabric layer, of the same material as the inner surface of the breast cup 10i, may be provided between the non-stretch layer 23 and the electrically conductive fabric portions 22a, 22b.

FIGS. 8a and 8b illustrate the center gore 20 (as shown in FIGS. 7a-7c) assembled with the breast cups 10L, 10R. In particular, FIG. 8a shows the center gore 20 attached between the lower edge region 30 of the breast cups 10L, 10R and the underwire casings 50a, 50b of those breast cups, thereby allowing the conductive fabric portions 22a, 22b to contact the underwire casings 50a, 50b and thus completing the electrical pathway from the underwire casing 50a of the left breast cup 10L to the first attachment transmitter point 25a and completing the electrical pathway from the underwire casing 50b of the right breast cup 10R to the second attachment point 25b (as shown in FIG. 8b).

It is preferred to fix the center gore 20 between the lower edge region 30 of the breast cups 10L, 10R and the underwire casings 50a, 50b, to provide a neat finish and to ensure a good electrical pathway between the underwire casings 50a, 50b and the electrically conductive fabric portions 22a, 22b of the center gore 20.

Figure 2D:
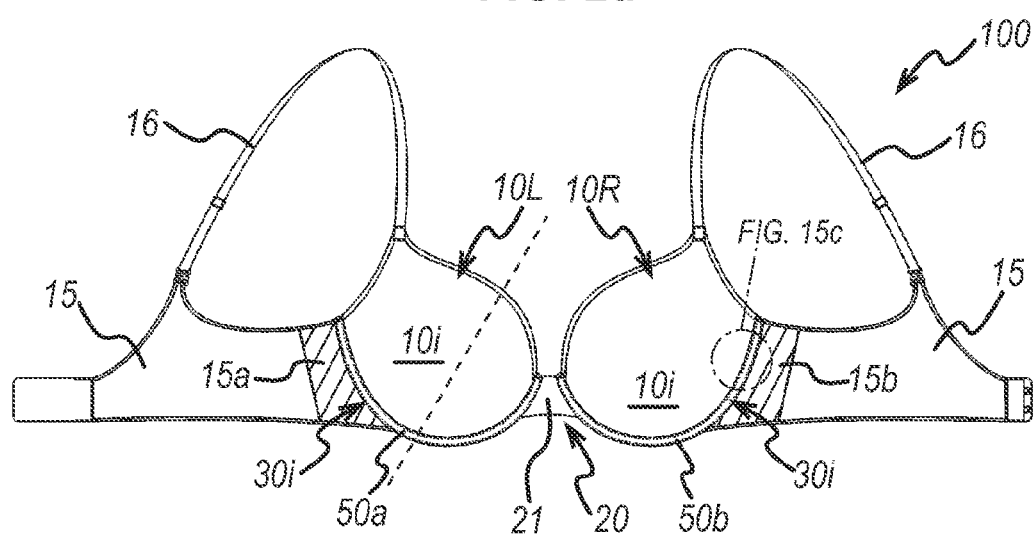
FIG. 2d shows a rear view of a bra according to an alternative embodiment of the present invention.
Figure 11A:
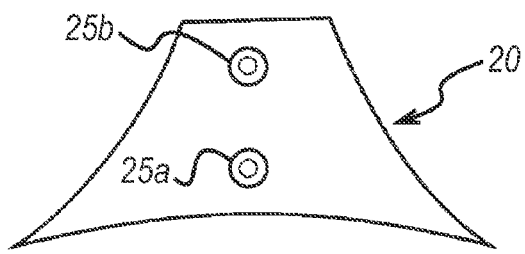
FIG. 11a is a front view of the center gore shown in FIG. 2d, in accordance with the present invention.
Figure 11B:
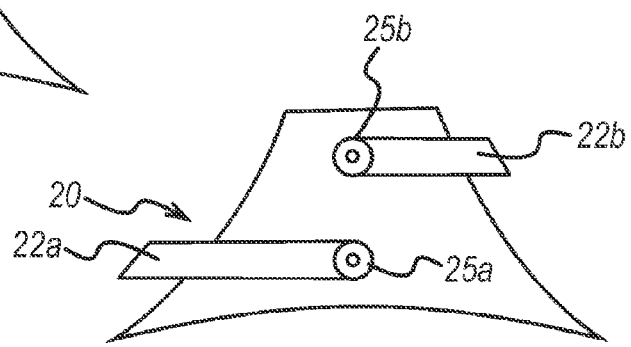
FIG. 11b is a back view of the center gore shown in FIG. 2d without showing the lower non-stretchable fabric layer and the lower fabric layer, in accordance with the present invention.
Figure 11C:
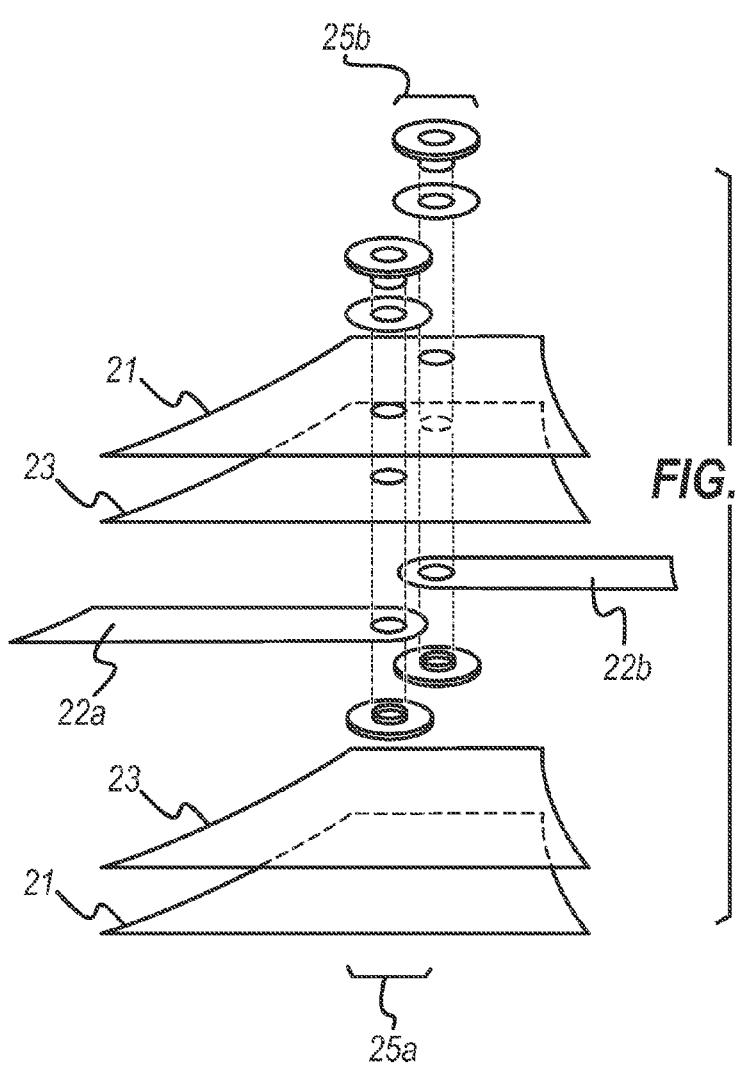
FIG. 11c is an exploded view of the components of the center gore shown in FIGS. 11a and 11b.
Figure 12A:
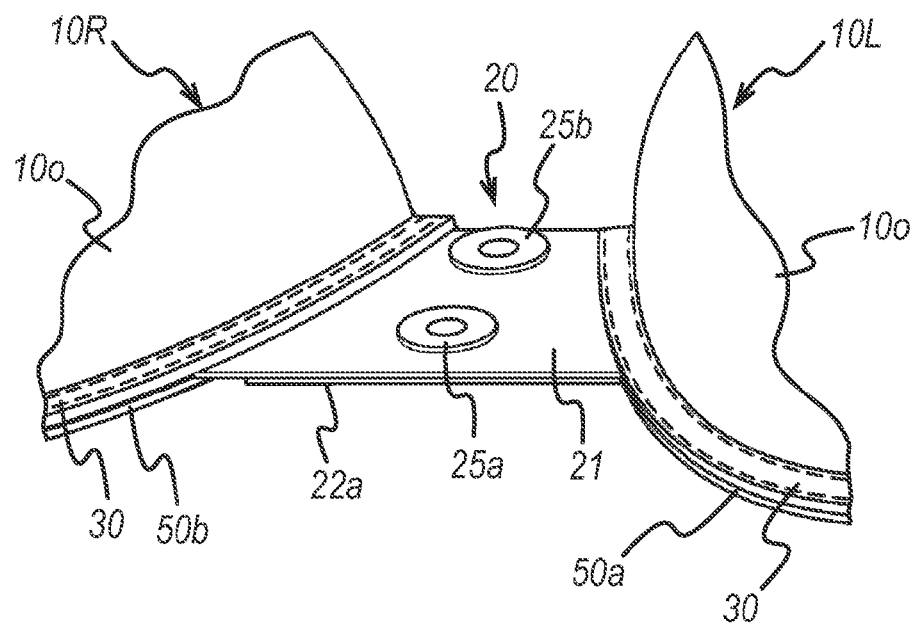
FIG. 12a is a front perspective view (taken from below) of the bra of FIG. 2d showing the center gore attached to the breast cups, in accordance with the present invention.
Figure 12B:
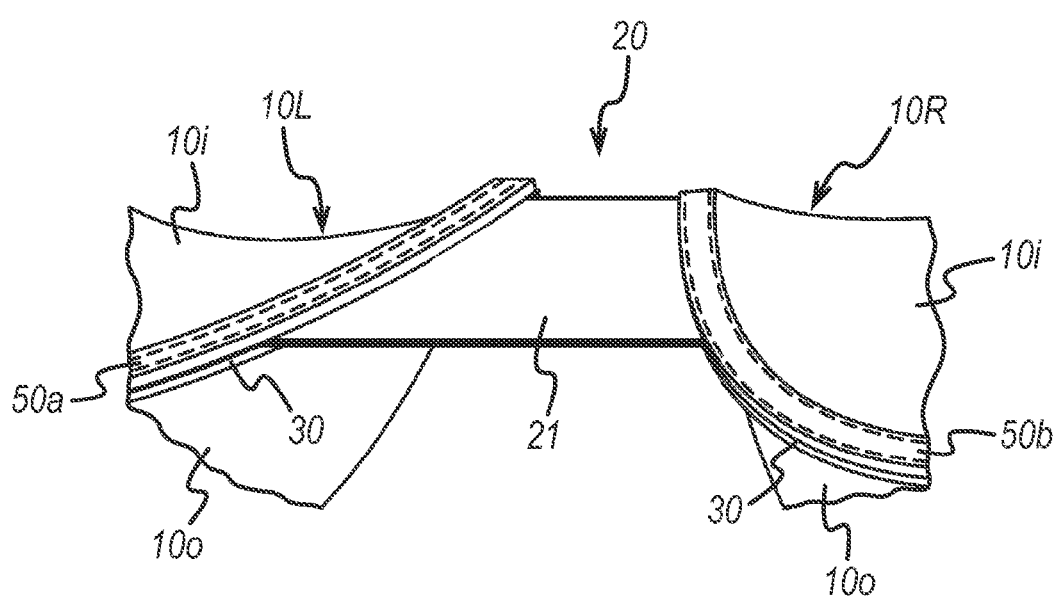
FIG. 12b is a back perspective view (taken from above) of the bra of FIG. 2d showing the center gore attached between the breast cups and underwire casings, in accordance with the present invention.

A variation of the embodiment of the center gore shown in FIGS. 2c, 7a-7c and 8a-8b is shown in FIGS. 2d, 11a-11c and 12a-12b. In this variation, as in particular shown in the exploded perspective view in FIG. 11c, the center gore 20 comprises an upper fabric layer 21 which is preferably of the same fabric as the outer surface 10o of the breast cups 10L, 10R, an optional upper non-stretchable fabric layer 23, the conductive fabric portions 22a, 22b, an optional lower non-stretchable fabric layer 23, and a lower fabric layer which is preferably of the same fabric as the inner surface 10i of the breast cups 10L, 10R. The lower fabric layer and optionally the lower non-stretchable fabric layer are present to prevent any "short-circuiting" that may occur through direct contact of the attachment points 25a, 25b or related conductive components with the human body. Thus, in this variation, the innermost side of the center gore, i.e. the side or surface that is in contact with the wearer's skin, preferably comprises fabric only. Thus, the difference between the gore of FIGS. 7a-c and the gore of FIGS. 11a-c is the addition of the lower fabric layer 21 and, optionally, the lower non-stretchable fabric layer 23. In addition, in this variation, the conductive fabric portions 22a, 22b preferably comprises thin strips of fabric as illustrated in FIGS. 11b and 11c, to save production cost. As shown in FIG. 2d, the inner surface of the sidewings 15 of the bra 100 optionally comprise electrically conductive fabric portions 15a, 15b to enhance the signal pickup, as described previously with respect to FIG. 2c.

Figure 13:
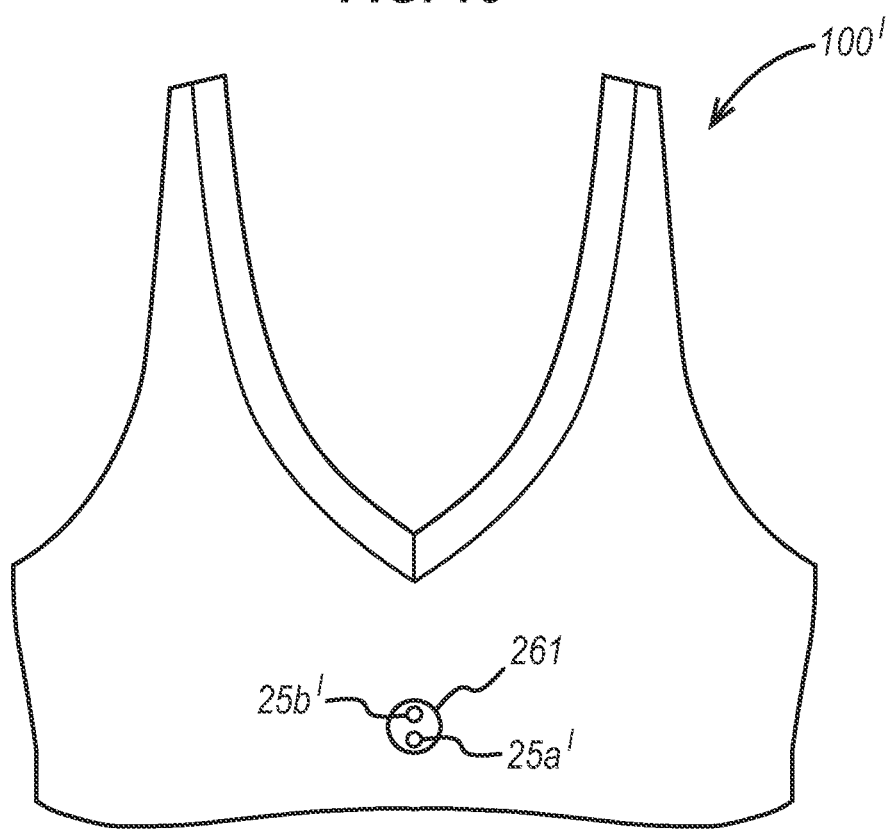
FIG. 13 shows a front view of a bra according to an embodiment of the present invention, without a transmitter attached to a center gore.

Another variation of an embodiment of a center gore which prevents or minimises "short circuiting", and a bra portion 100' comprising such a center gore, is now described with reference to FIGS. 13-16a. FIG. 13 shows a front (outside) view of a bra portion 100' comprising a center gore 20' having attachment points 25a', 25b' for a transmitter (not shown). The attachment points 25a', 25b' are conductive connectors for attaching to the transmitter (not shown), which in this embodiment, are magnetic connectors. Other fastener means, such as a snap-fit connector, are also possible. As shown, the outer surface of the bra optionally comprises a waterproof and/or insulating outer layer 26' which prevents or minimises short circuiting (across the attachment points 25a', 25b') due to moisture (e.g. sweat or rain) on the outer surface of the bra. The waterproof and/or insulating outer layer 26' is preferably a fabric, film or coating.

Figure 14A:
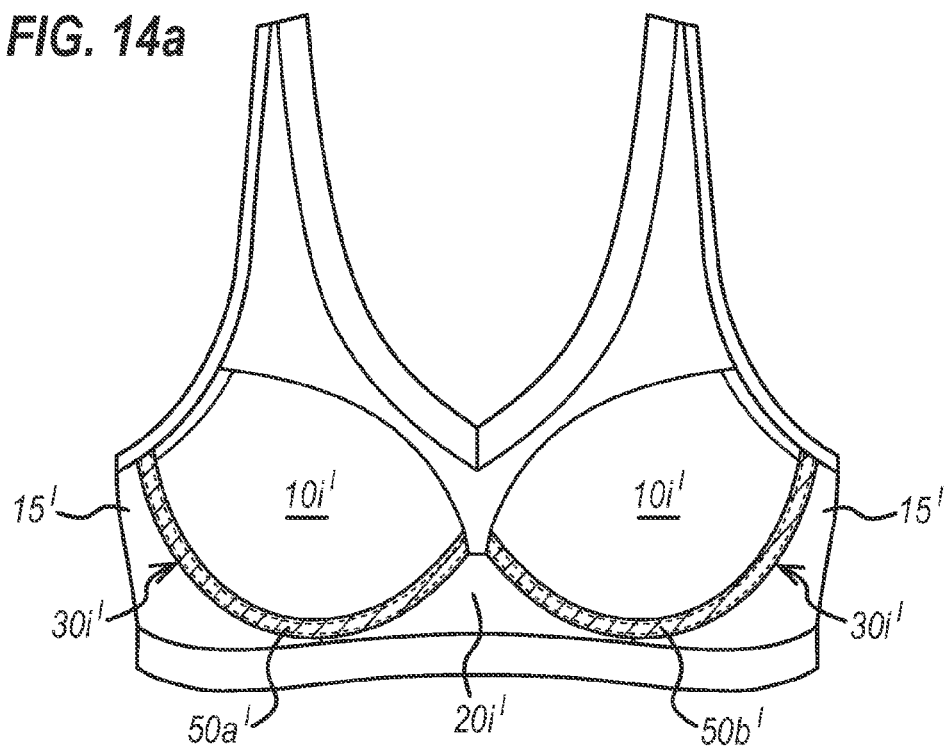
FIG. 14a shows a back view of the bra shown in FIG. 13.

FIG. 14a shows a back (inside) view of the bra portion 100' of FIG. 13. FIG. 15a shows an alternative back (inside) view of the bra portion 100' of FIG. 13. The bra portions 100' include a portion of the sidewing 15' attached to and extending from the breast cups 10i'. The difference between the bra portions of FIGS. 14a and 15a is that the bra portion 100' of FIG. 15a includes conductive fabric portions 15a', 15b' in the region of the sidewings 15' which attach to and extend from the breast cups, which will be described in more detail later, with reference to FIG. 15c.

Figure 14B:
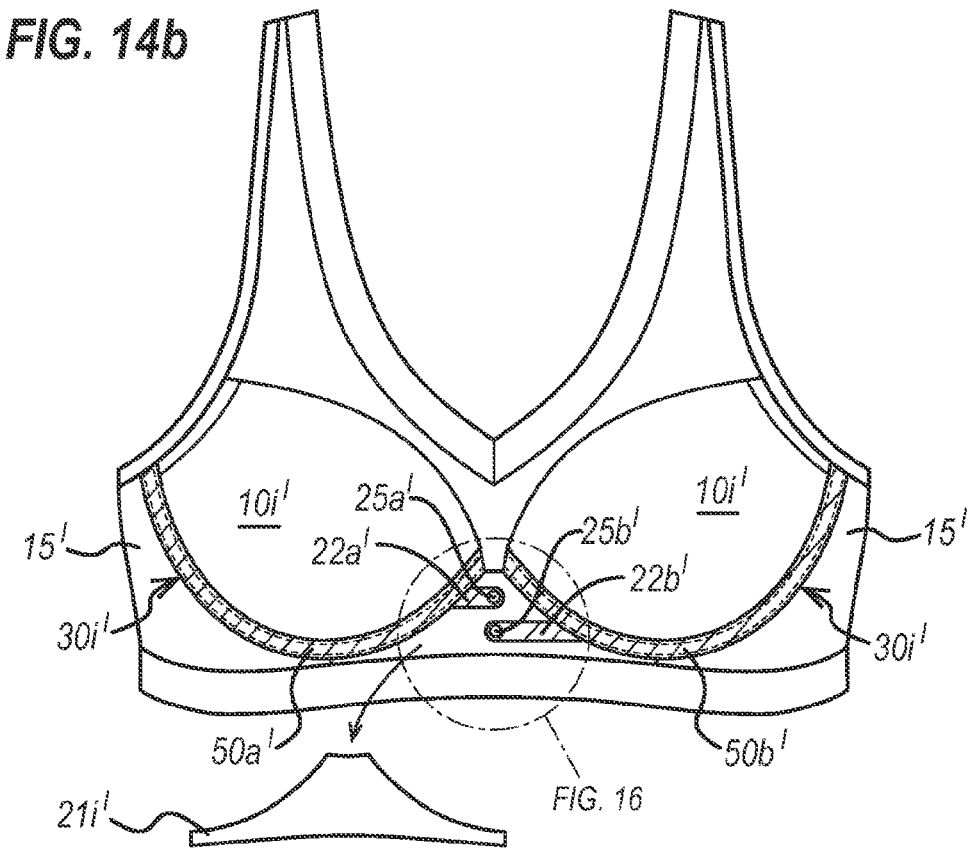
FIG. 14b shows the back view of FIG. 14a, with an inner fabric layer of the center gore removed to show the conductive fabric layer of the center gore.

As shown in FIGS. 14a and 15a, the bra portions 100' comprise, on the inner surface that contacts the wearer, conductive casings 50a', 50b' along the lower regions 30i' of the bra cups 10i' to pick up an electric signal from the wearer, as described previously with reference to FIGS. 2a-12b. Referring to FIGS. 14b and 15b, the bra portions 100' are shown with an inner layer 21i' of the center gore 20' removed, to show the conductive fabric portions 22a', 22b' of the center gore 20', which are substantially as described with reference to FIGS. 11b and 11c. Although the electrical pathway through the center gore 20' preferably consists of an electrically conductive fabric 22a', 22b', it will be understood that other electrical pathways may be provided, such as wires.

FIG. 16 shows the structure of the center gore 20' of the bra portion 100' of FIGS. 13 and 14a-b and the bra portion 100' of FIGS. 13 and 15a-b, as indicated in FIGS. 14b and 15b. The structure of the center gore 20' is the same for both bra portions 100'.

Referring to FIG. 16, the center gore 20' comprises an inner fabric layer 21i' (shown removed from the bra portion 100' in FIGS. 14b and 15b), an inner waterproof and/or insulating layer 23i', the electrically conductive fabric portions 22a', 22b', an outer waterproof and/or insulating layer 23o', an outer fabric layer 21o' and an additional outer fabric layer 24'. As shown, the gore 20' comprises electrically conductive button-type fasteners 25a', 25b' to couple (preferably magnetically) with a transmitter. The inner and outer fabric layers 21i', 21o' may comprise non-stretchable fabric, as described with respect to FIGS. 11a-c. An additional inner fabric layer (not shown) may be provided if desired, such that the difference between the gore 20' of FIG. 16 and the gore 20 shown in FIG. 11c is the addition of the waterproof and/or insulating layers 23i', 23o', 26'.

As shown in FIG. 16, the electrically conductive fabric portions 22a', 22b', and the inner parts of the button connectors 25a', 25b' are sandwiched between two insulating and/or waterproof layers 23i', 23o', preventing or minimising short circuiting between the inner parts of the connectors 25a', 25b' and the electrically conductive fabric portions 22a', 22b'.

The additional waterproof and/or insulating layer 26' provided between the outermost fabric layer 24' of the gore 20' and the outer surface of the attachment points 25a', 25b' prevents or minimises short circuiting across the outer parts of the button connectors 25a', 25b'. The outer additional waterproof and/or insulating layer 26' may not be required if the main moisture encountered is through sweat gathering on the inside of the bra.

Figure 16A:
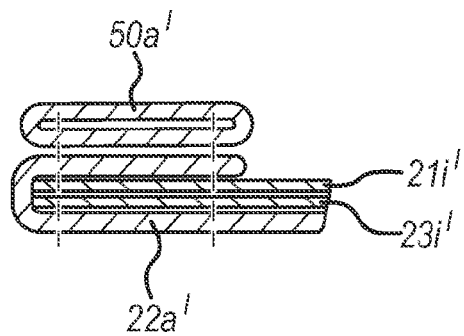
FIG. 16a, is a cross section of a layer structure as indicated on FIG. 16, showing a conductive component of the center gore wrapping around the inner layer(s) of the center gore to provide a conductive path with the electrically conductive underwire casing.

As stated previously, it is preferred to fix the center gore 20' between the lower edge region 30' of the breast cups 10i' and the underwire casings 50a', 50b', to provide a neat finish and to ensure a good electrical pathway between the underwire casings 50a', 50b' and the electrically conductive fabric portions 22a', 22b' of the center gore 20'. To achieve the electrical pathway when the electrically conductive fabric portions 22a', 22b' are sandwiched between the inner and outer waterproof and/or insulating layers 23i', 23o' and inner fabric layer 21i', the electrically conductive fabric portions 22a', 22b' are configured to extend beyond the inner waterproof and/or insulating layer 23i' and beyond the inner fabric layer 21i', and wrap around the edges of the inner waterproof and/or insulating layer 23i' and the inner fabric layer 21i', as shown in FIGS. 16 and 16a. Thus, the electrically conductive fabric portions 22a', 22b' are able to form an electrically pathway with the electrically conductive casings 50a', 50b'. As shown in FIGS. 16 and 16a, the layers of the gore 20' and each of the underwire casings 50a', 50b' are preferably sewn together (where the dashed lines represent sew lines).

As described previously, the difference between the bra portion 100' of FIGS. 14a-b and that of FIGS. 15a-b is the presence of electrically conductive fabric portions 15a', 15b' in the sidewing regions of the bra portion 100' of FIGS. 15a-b. FIG. 15c shows the layer structure of the sidewing of FIGS. 15a-b, where FIG. 15c shows a cross-section of a portion of FIG. 15b, as indicated. The underwire casing 50b' is sewn to the electrically conductive fabric portion 15b' of the sidewing, a foam layer 15f and an outer fabric layer 15o' of the sidewing. As described previously, the foam layer 15f increases the pressure felt in the sidewing enhancing the signal pick up, whilst also providing an even distribution of pressure in this region. The foam layer 15f preferably comprises a laminate of an outer fabric layer, a foam, and an inner fabric layer.

A cross-sectional view of the bra cup 10i' of the bra portion of FIGS. 13-16a (taken along the section shown in FIG. 18), looks substantially as shown in FIGS. 6a and 6b, where, with further reference to FIGS. 16 and 16a, the underwire casings 50a', 50b' are attached by sewing to the breast cups 10i', along the length of the upper and lower edges of the casings 50a', 50b' positioned on the inner surface 30i' of the lower edge region 30'. The sewing threads pass through the layers of the underwire casing 50a', 50b' and the lower region of the breast cups 10i'.

As described with reference to FIGS. 6a-6b, the breast cups 10i' may be formed of an inner foam layer 11, an outer foam layer 12, an inner fabric layer 13 and an outer fabric layer 14. The inner 13 and outer 14 fabric layers form the lower edge region of the breast cup (with or without one or more of the foam layers therebetween). The casings 50a', 50b' may house an underwire (not shown in FIG. 16a), if desired.

A preferred method of manufacturing a bra according to the present invention is therefore to first attach the center gore 20, 20' to the breast cups 10L, 10R, for example by sewing the center gore 20, 20' to the breast cups 10L, 10R at the inner portion (e.g. towards the cleavage area) of the lower edge regions 30, 30'. The sidewing or sidewings 15, 15' are then attached to the breast cup 10L, 10R along the outer portion (e.g. at the other end to the cleavage area) of the lower edge region 30, 30'. As will be understood, the sidewing(s) 15, 15' can equally be attached first, with the center gore 20, 20' attached afterwards. Furthermore, as will be understood by FIGS. 13, 14-b and 15a-b, at least a portion of the sidewing may be formed as a unitary piece with the bra cups. An additional sidewing portion may then be attached to the sidewing portion that was formed as a unitary piece with the breast cup.

As described above with reference to FIGS. 2c and 15a-c, the sidewings 15, 15' can comprise electrically conductive fabric portions 15a, 15b, 15a', 15b' at a region adjacent the breast cups 10i, 10i' to enhance signal pickup through increased contact area under firm pressure.

The next step is to attach the underwire casing 50a, 50b, 50a', 50b' to the breast cup along the lower edge region 30, 30'. As discussed previously, this can be achieved by sewing along the upper and lower edges of the underwire casing 50a, 50b, 50a', 50b' along the length of the lower edge regions 30, 30', as shown in FIGS. 2c, 2d, 8a, 8b, 12a, 12b, and 16. However, the underwire casing can be attached by any other suitable means.

The final step is to insert the underwire into the underwire casings (e.g. insert underwire 200, 300, 900 into casings 250, 350, 950) and sew across the ends of the casings 50a, 50b, 50a', 50b' to secure the underwires within the casings 50a, 50b, 50a', 50b'. If underwiring is not required, this step can be omitted.

The present invention also provides corresponding methods for manufacturing the bra components, i.e. the center gore 20, 20' and the underwire casings 250, 350, 950, as can be readily determined by analogy to the above bra component descriptions.

Alternative bras in accordance with the present invention are also provided. In a second embodiment of the present invention, the bra 100 comprises all of the features of the first embodiment as described with reference to FIGS. 2a-2d, 7a-7c, 8a-8b, 11a-11c, 12a-12b, and 13-16a, but a conductive fabric layer (or layers) is incorporated into or attached to the inner surface 30i, 30i' of the lower edge region 30, 30' of the breast cups 10L, 10R, instead of the underwire casing 50a, 50b, 50a', 50b'. Thus, the electrically conductive fabric layer provides the same function as the underwire casing, and is provided in the same location as the underwire casing, thus offering the same benefits as the underwire casing in terms of providing an electrical pathway for transmission of a signal to the transmitter. Electrical signals from the heart can be sensed and transmitted by the electrically conductive fabric of the lower edge region 30, 30' to the center gore 20, 20', through the electrically conductive fabric portions 22a, 22b. 22a'. 22b' of the center gore 20, 20', through the attachment points 25a, 25b, 25a', 25b' of the center gore and to the transmitter 70 (when attached).

The second embodiment of the present invention is therefore applicable to non-underwire bras and also molded bras which have the underwire (or optionally, underwire casing without an underwire) within the layers of the bra (rather than being attached to the outside of the breast cup at the lower edge region).

Figure 17A:
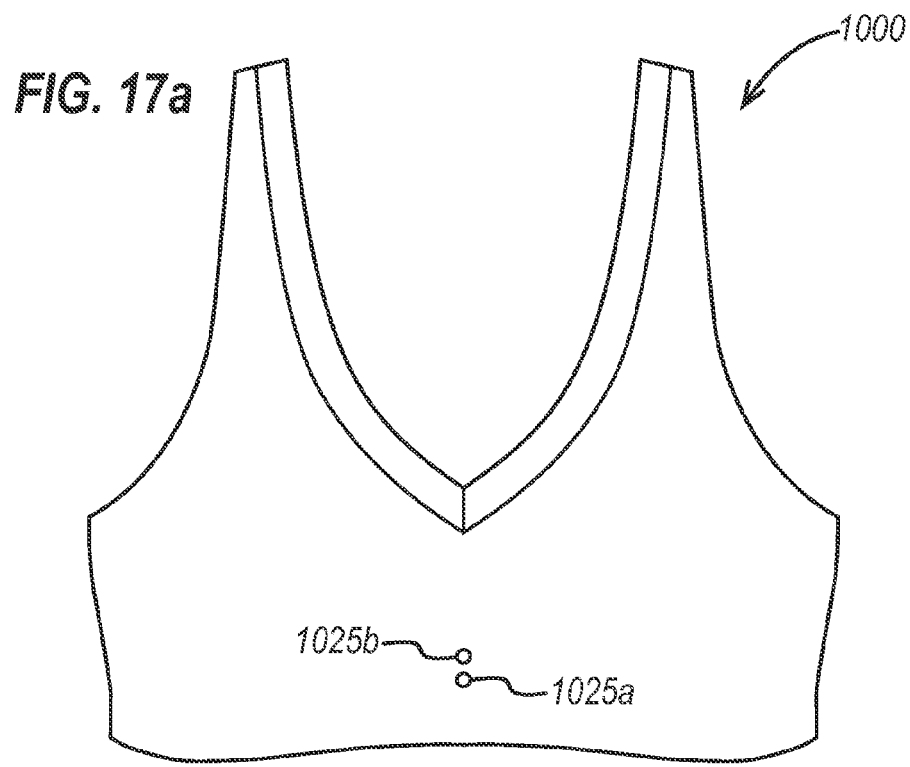
FIG. 17a shows a front view of a bra according to an embodiment of the present invention, without a transmitter attached to a center gore.

FIGS. 17a-20a illustrate molded bras or bra portions with an electrically conductive fabric layer attached, in accordance with the second embodiment of the invention. FIG. 17a shows a front (outside) view of a bra portion 1000 comprising a center gore 1020 having attachment points 1025a, 1025b for a transmitter (not shown). The attachment points 1025a, 1025b are conductive connectors for attaching to the transmitter, which in this embodiment, are magnetic connectors.

If desired, the outer surface of the bra 1000 may comprise a optional waterproof and/or insulating layer to prevent or minimise short circuiting across the outer parts of the attachment points 25a', 25b', as previously described with reference to FIGS. 13 and 16.

Figure 17B:
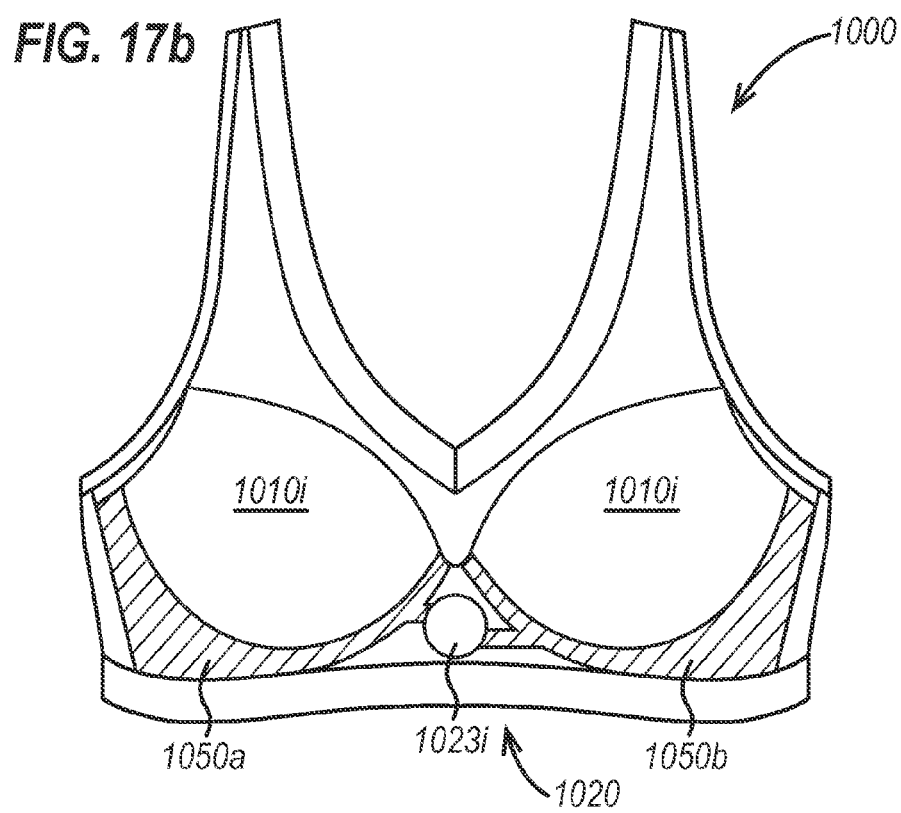
Figure 17C:
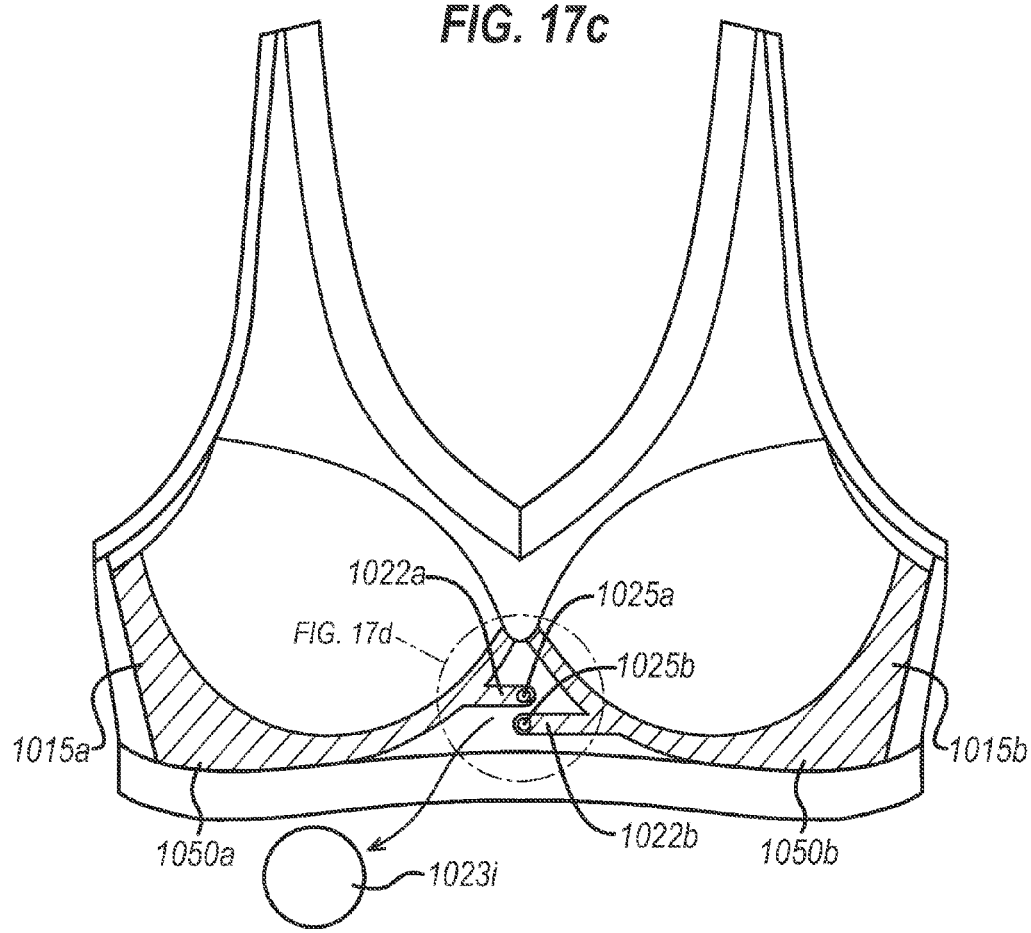
FIG. 17c shows the back view of FIG. 17b, with an inner layer of the center gore removed to show the conductive fabric layer of the center gore.
Figure 17D:
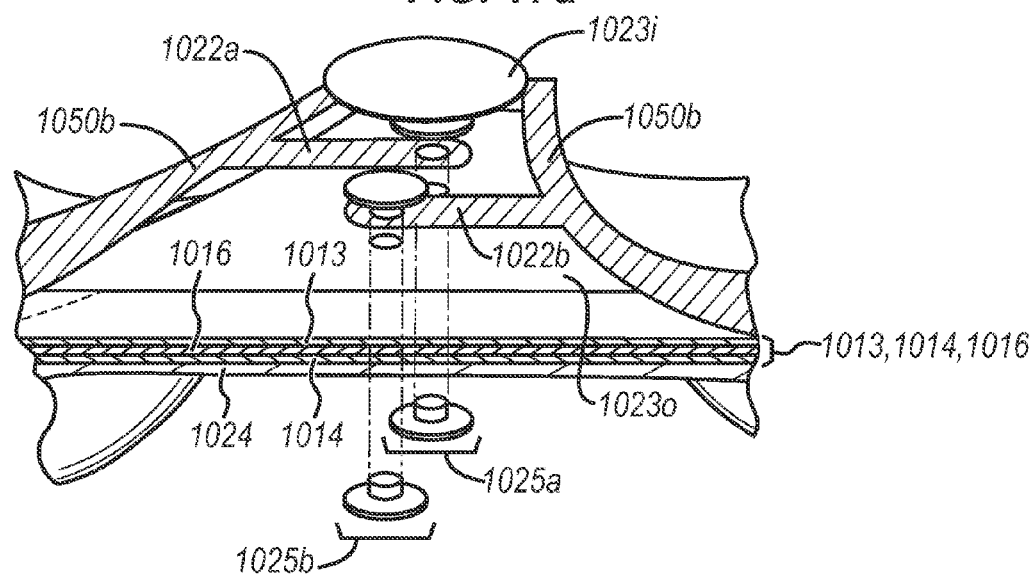
FIG. 17d is a front perspective exploded view (as indicated in FIG. 17c) of the bra of FIGS. 17a-c, showing the center gore components, the underwire casings and the breast cups, in accordance with the present invention.

The back, inner view of the bra portion 1000 is shown in FIGS. 17b and 17c. As shown in FIGS. 17b and 17c, the bra 1000 comprises conductive fabric portions 1050a, 1050b attached to the inner surface of the bra, along the lower periphery of each breast cup 1010i. As shown, the conductive fabric portions 1050a, 1050b may extend into the sidewing regions 1015a, 1015b, as described previously with respect to FIG. 15b. FIG. 17c shows the back, inner, view of the bra portion 1000 of FIG. 17b, with an inner layer 1023i of the central gore 1020 removed to expose the inner parts of the attachment points 1025a, 1025b and to fully expose the conductive fabric portions 1050a, 1050b. As shown in FIG. 17c, the conductive fabric layer is formed of two parts, corresponding to a part 1050a, 1050b for each breast cup 1010i, the conductive fabric portions 1022a, 1022b extending to the attachment points and corresponding sidewing region 1015a, 1015b. The inner layer 1023i is an insulating and/or waterproof layer to prevent or minimise short circuiting across the attachment points 1025a, 1025b and the conductive fabric portions 1022a, 1022b extending to the attachment points.

FIG. 17d shows an exploded perspective view of the center gore 1020 region as indicated in FIG. 17c. The bra 1000 is a molded bra, which can be formed by molding multiple fabric and foam layers under heat and pressure. As will be understood from FIGS. 17c and 17d, the bra portion 1000 can be formed as a unitary piece, comprising an inner fabric layer 1013 and an outer fabric layer 1014 that together form the inner and outer layers of the center gore 1020 and the bra cups. Additional foam layers may be provided in the structure, for example between the inner and outer fabric layers 1013, 1014 of the gore 1020, as shown in FIG. 17d (layer 1016) or between the inner and outer fabric layers 13, 14 of the breast cups, as shown in FIGS. 19-20a (layers 11 and 12). Returning to FIG. 17d, the gore 1020 comprises an outer waterproof and/or insulating layer 1023o, with the conductive fabric portions 1022a, 1022b and the attachment points 1025a, 1025b being sandwiched between the inner and outer waterproof and/or insulating layers 1023i, 1023o. As shown in FIG. 17d, the gore 1020 may further comprise an outer fabric layer 1024.

The foam layer 1016 of the fabric-foam laminate 1013, 1014, 1016 may act as an insulating layer to minimise or prevent short circuiting, making an outer waterproof and/or insulating layer (as described with reference to FIG. 16) unnecessary.

FIGS. 19a-20a illustrate a cross-section through the bra cup of FIGS. 17a-d, taken along the line shown in FIG. 18. FIG. 19 and FIG. 20 illustrate two different underwire configurations 1350, 1350' which are formed within the molded bra. FIG. 19 shows a bra cup, much as shown in FIGS. 6a and 6b, having an inner fabric layer 13, and outer fabric layer 14, and two foam layers 11, 12 sandwiched therebetween. The cross-sections differ due to the underwire or underwire casings shown. FIGS. 19 and 19a show an underwire casing 1320 between the inner and outer foam layers 11, 12, which may or may not comprise an underwire 1330. The underwire casing may be made of TPR (thermoplastic rubber), PP (polypropylene), nylon, TPU (thermoplastic polyurethane), TPE (thermoplastic elastomer), TPEE (thermoplastic polyester elastomer), non-elastic fabric, or any other suitable material.

FIGS. 20 and 20a show a cushioned plastic underwire 1350' sandwiched between the inner and outer fabric layers 11, 12. The cushioned plastic underwire 1350' may comprise a polypropylene underwire 1330' encased in thermoplastic rubber casing 1320'.

For both cross-sections, the breast cups are provided with an electrically conductive fabric layer 1050a, 1050b at their lower periphery, as illustrated in FIGS. 17b and 17c. The electrically conductive fabric layer 1050a, 1050b may be attached by any suitable means. In the preferred embodiment, the electrically conductive fabric layer 1050a, 1050b is attached with adhesive 151.

The bra in accordance with the second embodiment may be manufactured in the same way as the first embodiment. In particular, the center gore 20 may first be attached to the breast cups 10L, 10R; the sidewing or sidewings 15 are attached to the breast cups 10L, 10R, before or after attachment of the central gore 20; and the conductive fabric layer is attached to the breast cup along the lower edge region 30. As discussed previously, this can be achieved by sewing along the upper and lower edges of the electrically conductive fabric layer or layers. If the lower edge region of the breast cups is provided with electrically conductive fabric (e.g. by incorporating electrically conductive yarn), the last step is not required.

Alternatively, as described with respect to FIGS. 17-20, a bra portion 1000 comprising breast cups, center gore 1020 and sidewing regions can be formed as a unitary piece in a molding process, with the electrically conductive fabric layer 1050a, 1050b being attached thereafter, followed by the attachment of the attachment points 1025a, 1025b, and the waterproof and/or insulating film, coating or fabric 1023i.

By providing the sensors as conductive fabric attached to or incorporated within the inner surface of the lower edge regions of the breast cups, there is the ability to enhance the picking up of the heart rate signal and reduce the loss of signal since the sensors fit the wearer's body well and the sensors are well located. As discussed above, this may be achieved by attaching an underwire casing comprising an electrically conductive fabric to the lower edge regions or by providing the lower edge regions with an electrically conductive fabric (e.g. by incorporating electrically conductive yarn into the lower edge regions or attaching an electrically conductive fabric layer to the lower edge regions).

It will be appreciated that this description is by way of example only; alterations and modifications may be made to the described embodiment without departing from the scope of the invention as defined in the claims.

The invention claimed is:

1. An underwire casing for a bra, the underwire casing comprising:
    an electrically conductive fabric layer, separate from a fabric of the bra, comprising an underwire casing, the electrically conductive fabric layer having a length that extends longitudinally along a lower edge region of a first breast cup, wherein the electrically conductive fabric layer is adapted to contact a wearer's skin throughout its length.

2. The underwire casing of claim 1, further comprising an underwire disposed in the electrically conductive fabric layer comprising the underwire casing.

3. A breast cup for a bra, the breast cup having:
    an inner surface adapted to contact a wearer's body when worn,
    an outer surface facing away from the wearer's body when worn, and
    a lower edge region dimensioned and arranged to follow a shape of a breast of the wearer,
    wherein the lower edge region is arranged below the wearer's breast and comprises an electrically conductive fabric layer on the inner surface,
    wherein the electrically conductive fabric layer has a length that extends longitudinally along the lower edge region of the breast cup and is further adapted to contact skin of the wearer throughout its length.

4. The breast cup of claim 3, wherein the the electrically conductive fabric layer comprises an underwire casing attached to the inner surface of the lower edge region.

5. A bra having an inner surface which is in contact with a wearer's body when worn, and an outer surface which faces away from the wearer's body when worn, wherein the bra comprises:
    a left breast cup;
    a right breast cup; and
    a center gore attached between the left and right breast cups;
    wherein each of the left and right breast cups comprises a lower edge region which is shaped to follow the shape of a wearer's breast and is shaped to be positioned below a wearer's breast to support the breast, and wherein the lower edge region comprises an electrically conductive fabric layer on the inner surface for contact with the wearer's skin;
    wherein the center gore comprises:
    an attachment area for attachment of a transmitter; and
    an electrically conductive pathway from the electrically conductive fabric of the lower edge regions of the breast cups to the attachment area.

6. The bra of claim 5, wherein the center gore comprises an outer layer and an inner layer, and the electrically conductive pathway is positioned between the inner and outer layers.

7. The bra of claim 6, wherein at least one of the inner and outer layers is at least one of waterproof and electrically insulating.

8. The bra of claim 6, wherein at least one of the inner and outer layers is a fabric layer, a coating, or a film.

9. The bra of claim 5, wherein the center gore comprises an electrically conductive fabric layer which forms the electrically conductive pathway from the electrically conductive fabric of the lower edge regions of the breast cups to the attachment area.

10. The bra of claim 9, wherein the electrically conductive fabric layer of the gore is on the inner surface of the gore, in contact with the wearer's body when worn.

11. The bra of claim 9, wherein the center gore comprises an outer layer and an inner layer, and the electrically conductive fabric is positioned between the inner and outer layers.

12. The bra of claim 11, wherein a portion of the electrically conductive fabric layer of the gore extends beyond the inner layer and folds over the inner layer, such that the electrically conductive layer of the gore contacts the electrically conductive fabric layer of the lower edge region of the breast cups.

13. The bra of claim 9, wherein the center gore comprises a first attachment point and a second attachment point, wherein the electrically conductive fabric layer is in two portions, a first portion which passes from the electrically conductive fabric layer of the left breast cup to the first attachment point and a second portion which passes from the electrically conductive fabric layer of the right breast cup to the second attachment point.

14. The bra of claim 5, wherein the bra further comprises:
    at least one sidewing attached to and extending from at least one of the left and right breast cups;
    wherein the at least one sidewing comprises an electrically conductive fabric layer on at least a portion of the inner surface in contact with the wearer when the bra is worn.

15. The bra of claim 5, wherein the electrically conductive fabric layer of each breast cup further comprises an underwire casing attached to the inner surface of the lower edge region.

16. A center gore for attaching together two breast cups for a bra, the center gore comprising an attachment area for attaching a transmitter and a layer of electrically conductive fabric for transmitting an electrical signal to the attachment area, the attachment area having an electrically conductive attachment point contacting the layer of electrically conductive fabric, the electrically conductive attachment point for receiving the electrical signal transmitted to the attachment area by the layer of electrically conductive fabric and transmitting the electrical signal to the transmitter.

17. The center gore of claim 16, comprising an outer layer and an inner layer, wherein the layer of electrically conductive fabric is positioned between the inner and outer layers.

18. The center gore of claim 17, wherein at least one of the inner and outer layers is at least one of waterproof and electrically insulating.

19. The center gore of claim 17, wherein a portion of the electrically conductive fabric layer extends beyond the inner layer and folds over the inner layer.

20. The center gore of claim 16, wherein the electrically conductive fabric layer of the gore is on the inner surface of the gore, in contact with the wearer's body when worn.

21. An underwire casing for a bra, the underwire casing comprising:
- a fabric casing for receiving an underwire, the fabric casing having a length that extends longitudinally along a lower edge region of a first breast cup; and
- an electrically conductive fabric layer, separate from a fabric of the bra, wrapped around the fabric casing, the electrically conductive fabric layer for contacting a wearer's skin along the length of the fabric casing.

* * * * *